United States Patent
Karlsson et al.

(10) Patent No.: US 7,344,891 B2
(45) Date of Patent: Mar. 18, 2008

(54) PROCESS VESSEL WITH INTEGRAL EVAPORATOR

(75) Inventors: Arne Karlsson, Oslo (NO); Ivar M. Dahl, Oslo (NO); Jonny Engedahl, Oslo (NO); Mark A. Krawczyk, Chicago, IL (US); Ara J. Alexanian, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 468 days.

(21) Appl. No.: 11/033,567

(22) Filed: Jan. 11, 2005

(65) Prior Publication Data

US 2005/0158216 A1  Jul. 21, 2005

Related U.S. Application Data

(62) Division of application No. 10/095,879, filed on Mar. 12, 2002.

(51) Int. Cl.
*G01N 1/10* (2006.01)
(52) U.S. Cl. ............... 436/180; 422/99; 422/100; 422/101; 422/102; 422/104; 436/37
(58) Field of Classification Search .......... 422/99–101, 422/102, 104; 436/180, 37
See application file for complete search history.

(56) References Cited

U.S. PATENT DOCUMENTS

| 3,359,074 | A |   | 12/1967 | Dobo ..................... 23/283 |
|---|---|---|---|---|
| 3,929,421 | A | * | 12/1975 | Werges ..................... 422/193 |
| 5,037,619 | A | * | 8/1991 | Alagy et al. ............... 422/191 |
| 5,453,256 | A |   | 9/1995 | Rumpf et al. ............. 422/211 |
| 5,453,526 | A |   | 9/1995 | Pinnavaia .................. 556/32 |
| 5,612,002 | A |   | 3/1997 | Cody et al. ................ 422/131 |
| 5,766,556 | A |   | 6/1998 | DeWitt et al. ............. 422/131 |
| 6,342,185 | B1 | * | 1/2002 | Dahl et al. ............... 422/82.12 |
| 6,551,832 | B1 |   | 4/2003 | Deves et al. ................ 436/37 |

FOREIGN PATENT DOCUMENTS

| EP | 0861 802 A2 | 2/1998 |
|---|---|---|
| EP | 1072 866 A1 | 5/2000 |
| EP | 1108467 A2 | 6/2001 |

(Continued)

OTHER PUBLICATIONS

Akporiaye, D.E.; Dahl, I.M.; Karlsson, A.; Wendelbo, R. *Angew Chem. Int. Ed.* 1998, 37, 9-611.

(Continued)

*Primary Examiner*—Jill Warden
*Assistant Examiner*—Jyoti Nagpaul
(74) *Attorney, Agent, or Firm*—Maryann Maas

(57) ABSTRACT

A process vessel containing both an evaporation zone for evaporating a liquid feed and a treatment zone for treating the resulting vapor comprises an injector having an orifice, the orifice being in the evaporation zone, at least one evaporation surface for evaporating feed and generating vapor, the evaporation surface being located in the evaporation zone, wherein the injector orifice and the evaporation surface are positioned to prevent the formation of a drop at the orifice, a treatment zone for treating the vapor and at least one heater associated with at least a portion of the process vessel.

14 Claims, 6 Drawing Sheets

FOREIGN PATENT DOCUMENTS

| | | |
|---|---|---|
| FR | EP1072886 A1 | 1/2001 |
| RU | 1290597 | 9/1994 |
| SU | 1489825 | 6/1989 |
| SU | 1549580 | 3/1990 |
| SU | 1641414 | 4/1991 |
| WO | WO 97/32208 | 9/1997 |
| WO | WO 98/07026 | 2/1998 |
| WO | WO 98/36826 | 8/1998 |
| WO | WO 99/19724 | 4/1999 |
| WO | WO 99/34206 | 7/1999 |
| WO | WO 02/092220 A1 | 11/2002 |
| WO | WO 02 092221 A | 11/2002 |

OTHER PUBLICATIONS

Bein, T. *Angew. Chem. Int. Ed.*, 1999, 38(3) 323-326.

Bej, K.S.; Rao, J.S. Ind. Eng. Chem. Res., 1991 30 (8). 1819-1832.

Cong, P.; Doolen, R.D.; Fan, Q.; Giaquinta, D.M.; Guan, S.; McFarland, E.W.; Poojary, D.M.; Self, K.; Turner, H.W.; Weinberg, W.H. *Angew Chem. Int. Ed. 1999*, 38 (4) 484-488.

Eliezer K.F.; Bhinde, J.; Houalla, M.; Broderick, D.; Gates, B.C.; Katzer, J.R.; Olson, J.H. Ind. Eng. Chem. Fundam., 1977, 16 (3), 380-384.

Holzwarth, A.: Schmodt, H.; Maier, W.F. *Angew. Chem. Int. Ed.*, 1998, 37(9) 2644-2647.

Klein, J.; Lehmann, D.W.; Schmidt, H.; Maier, W.F. *Angew Chem. Int. Ed.* 1998, 37 (24), 3369-3372.

Senkan, S.M. *Nature*, Jul. 1998, 394(23), 350-353.

Taylor, S.J.; Morken, J.P. *Science*, Appr. 1998, 280 (10), 267-270.

Font, R.; Marcilla, A; Verdu, E.; Devesa, J.; *Ind. Eng. Chem. Prod. Res. Dev.* 1986 (25) 491-498.

* cited by examiner

PROCESS VESSEL WITH INTEGRAL EVAPORATOR

CROSS-REFERENCE TO RELATED APPLICATION

This application is a Division of copending application Ser. No. 10/095,879 filed Mar. 12, 2002, the contents of which are hereby incorporated by reference in its entirety.

FIELD OF THE INVENTION

The present invention relates to one or more process vessels each process vessel containing both a treatment zone and an evaporation zone; the evaporation zone for vaporizing a liquid feed within the process vessel. The present invention also relates to a single, sequential, or parallel process of vaporizing a liquid feed within the process vessel(s).

BACKGROUND OF THE INVENTION

Before a catalyst is selected for use in a commercial application, for example hydrocarbon reactions in petroleum refining, a great number of catalysts may be examined for use in the envisioned application. A large number of newly synthesized catalytic compositions may be considered as candidates. It then becomes important to evaluate each of the potential catalysts to determine the formulations that are the most successful in catalyzing the reaction of interest under a given set of reaction conditions.

Two key characteristics of a catalyst that are determinative of its success are the activity of that catalyst and the selectivity of the catalyst. The term activity refers to the rate of conversion of reactants by a given amount of catalyst under specified conditions, and the term selectivity refers to the degree to which a given catalyst favors one reaction compared with another possible reaction, see, *McGraw-Hill Concise Encyclopedia of Science and Technology*, Parker, S. B., Ed. in Chief; McGraw-Hill: New York, 1984; p. 8.

The traditional approach to evaluating the activity and selectivity of new catalysts is a sequential one. When using a micro-reactor or pilot plant, each catalyst is independently tested at a set of specified conditions. Upon completion of the test at each of the set of specified conditions, the current catalyst is removed from the micro-reactor or pilot plant and the next catalyst is loaded. The testing is repeated on the freshly loaded catalyst. The process is repeated sequentially for each of the catalyst formulations. Overall, the process of testing all new catalyst formulations is a lengthy process at best.

Combinatorial chemistry deals mainly with the synthesis of new compounds. For example, U.S. Pat. No. 5,612,002 B1 and U.S. Pat. No. 5,766,556 B1 teach an apparatus and a method for simultaneous synthesis of multiple compounds. Akporiaye, D. E.; Dahl, I. M.; Karlsson, A.; Wendelbo, R. *Angew Chem. Int. Ed.* 1998, 37, 9-611 disclose a combinatorial approach to the hydrothermal synthesis of zeolites, see also WO 98/36826.

Combinatorial methods present the possibility of substantially increasing the efficiency of catalyst evaluation. Recently, efforts have been made to use combinatorial methods to increase the efficiency and decrease the time necessary for thorough catalyst testing. For example, WO 97/32208-A1 teaches placing different catalysts in a multi-cell holder with the heat absorbed or liberated in each cell being measured to determine the extent of each reaction. Thermal imaging has also been used; see Holzwarth, A.; Schmodt, H.; Maier, W. F. *Angew. Chem. Int. Ed.*, 1998, 37, -47, and Bein, T. *Angew. Chem. Int. Ed.*, 1999, 3-3. Measuring the heat absorption or liberation and thermal imaging may provide semi-quantitative data regarding activity of the catalyst in question, but they provide no information about selectivity.

Some attempts to acquire information as to the reaction products in rapid-throughput catalyst testing are described in Senkan, S. M. *Nature*, July 1998, 4(23), 3-353, where laser-induced resonance-enhanced multiphoton ionization is used to analyze a gas flow from each of the fixed catalyst sites. Similarly, Cong, P.; Doolen, R. D.; Fan, Q.; Giaquinta, D. M.; Guan, S.; McFarland, E. W.; Poojary, D. M.; Self, K.; Turner, H. W.; Weinberg, W. H. *Angew Chem. Int. Ed.* 1999, 4-8 teach using a probe with concentric tubing for gas delivery/removal and sampling. Only the fixed bed of catalyst being tested is exposed to the reactant stream, with the excess reactants being removed via vacuum. The single fixed bed of catalyst being tested is heated and the gas mixture directly above the catalyst is sampled and sent to a mass spectrometer.

Attempts have been made to apply combinatorial chemistry to evaluate the activity of catalysts. Some applications have focused on determining the relative activity of catalysts in a library; see Klien, J.; Lehmann, C. W.; Schmidt, H.; Maier, W. F. *Angew Chem. Int. Ed.* 1998, 37, 39-3372; Taylor, S. J.; Morken, J. P. *Science*, April 1998, 0(10), 7-270; and WO 99/34206-A1. Some applications have broadened the information sought to include the selectivity of catalysts. WO 99/19724-A1 discloses screening for activities and selectivities of catalyst libraries having addressable test sites by contacting potential catalysts at the test sites with reactant streams forming product plumes. The product plumes are screened by passing a radiation beam of an energy level to promote photoions and photoelectrons which are detected by microelectrode collection. WO 98/07026-A1 discloses miniaturized reactors where the reaction mixture is analyzed during the reaction time using spectroscopic analysis.

In order to determine the activity and selectivity of multiple catalysts, arrays of reactors have been designed to simultaneously examine multiple catalysts using the above mentioned analysis techniques. For example, EP 1108467 A2 teaches reactors with removable sections to allow easy introduction of catalyst to the reactor bed. The reactors are sealed using o-rings to allow quick connection of the reactor parts and also provide a reliable seal between the reactor parts and between each reactor and its environment.

Many reactors available currently are designed for the situation where the feed streams are all of the same phase, for example two feed components that are both gases. Many process technologies and chemistries require higher-pressure gas-phase catalysis, in which a liquid feedstock is vaporized before contacting the catalyst. This may become challenging due to the fact that many seals used for combinatorial arrays have a temperature limitation that is below the bubble point of many reactor inlet compositional mixtures. For example, the long-term temperature limitation on a typical O-ring seal is about 170° C., while the bubble point of $C_6$ to $C_9$ hydrocarbons, for example toluene, at operating pressures of about 300 psig (2172 kPa) to about 450 psig (3220 kPa) are between about 180° C. and about 240° C. at a hydrogen to toluene molar ratio between about 1 and about 3.

U.S. Pat. No. 5,453,526 B1 teaches a catalytic reactor where liquid media can be continuously introduced, evaporated, and fed to a catalytic reaction. U.S. Pat. No. 3,359,074 teaches a polycondensation system of a single vertically extending column which is transversely partitioned to define, in descending order, a reaction chamber, an evaporator chamber, and a finishing chamber. Two articles, Bej K. S.; Rao, M. S. Ind. Eng. Chem. Res., 1991 30 (8), 1819-1832, and Eliezer K. F.; Bhinde, M.; Houalla, M.; Broderick, D.; Gates, B. C.; Katzer, J. R.; Olson, J. H. Ind. Eng. Chem. Fundam., 1977, 16 (3), 380-385 show where additional particles are used to aid in flow distribution before a feed is contacted with a catalyst. What is needed is an evaporator that can be integrated into a process vessel, that accommodates a liquid feed so that the seals will not be compromised during operation of the process vessel, while providing for the feed to be in a vapor phase during reaction.

However, evaporators in general have some inherent problems associated with their operation. One problem associated with evaporators in general is non-uniform mixing of a liquid feed and a gas feed. Non-uniform mixing may occur when both a gas and a liquid are introduced to an evaporator through a common inlet. The dual feed of liquid and gas causes alternating regions of gas entrainment and liquid pulsation being introduced to an evaporator, and therefore regions of low concentration of the vaporized species followed by regions of high concentration of the vaporized species being sent to a reactor bed.

Another problem associated with non-uniform vaporization occurs mainly because of a non-uniform flow of liquid into an evaporator. In the case of slower moving flow, a liquid issuing from an orifice into an evaporator can form droplets that detach at a regular periodicity because of the fluid dynamics of the liquid. The periodic formation and detachment of droplets leads to non-uniform vaporization within the evaporator.

What is needed is an evaporator for use in a process vessel that overcomes the problems of non-uniform mixing and non-uniform vaporization associated with evaporators in general.

BRIEF SUMMARY OF THE INVENTION

It is an object of the present invention to provide a process vessel for vaporizing a liquid feed and treating the resulting vapor in the process vessel. It is further an object of the present invention to provide a process of vaporizing a liquid feed and treating the vapor within the process vessel.

In accordance with the present invention, a process vessel is provided for vaporizing a liquid feed within an evaporation zone before processing the feed in a treatment zone of the process vessel. The process vessel includes an evaporation zone, an injector having an orifice for injecting the liquid feed into the evaporation zone, at least one evaporation surface, a treatment zone, and a heater associated with a portion of the process vessel. The evaporation surface and the injector orifice are positioned within the evaporation zone so that the evaporation surface interferes with the formation of a drop of liquid feed at the orifice and a thin liquid film of the liquid feed is created on the evaporation surface. The heater heats the liquid feed within the evaporation zone to a temperature sufficient to vaporize the liquid feed. It is preferred that the evaporation surface be a bed of packing.

Further in accordance with the present invention, a process is provided for vaporizing a liquid feed within the process vessel. The inventive process includes the steps of providing at least one evaporation surface in an evaporation zone of the process vessel, injecting a liquid feed into the evaporation zone through an injector orifice, heating and vaporizing the liquid feed within the evaporation zone of the process vessel. A gap formed between the injector orifice and the evaporation surface is sufficiently small so that the evaporation surface interferes with the formation of a drop of liquid feed at the orifice. The liquid feed is instead directed to form a thin liquid film on the evaporation surface which facilitates uniform vaporization and uniform concentration in the resulting vapor. The vaporized feed is flowed to a treatment zone of the process vessel and treated within the treatment zone to generate an effluent. It is preferred that the evaporation surface be a bed of packing.

DETAILED DESCRIPTION OF THE INVENTION

For ease of understanding, the present invention will be explained below in terms of the preferred embodiment where the process vessel is a reactor having an evaporation zone and a reaction zone. It must be understood however, that other vessels are within the generally broad scope of the invention. Furthermore, other treatment zones in addition to a reaction zone are within the generally broad scope of the invention. Referring to the figures, there is shown a novel and improved reactor 10 for evaporating liquid feed to form a vapor and reacting said feed in the presence of catalyst to make a product. The inventive reactor 10 prevents seals 28 and 30 and from being compromised and maintains a reliable seal between reactor 10 and the environment while also providing for a liquid feed to be vaporized within reactor 10 as required by a reaction. Reactor 10 is particularly useful for evaluation of a catalyst 24 for a particular reaction. The inventive reactor 10 may also be used in an array 120 for the simultaneous reaction of a liquid feed in the presence of several catalysts and for the evaluation of multiple catalysts in a combinatorial method. The integrated vaporization of the liquid feed within the reactor makes reactor 10 more versatile than previous reactors used for the combinatorial process because it allows for a liquid component to be introduced to reactor 10, even if it needs to be in the vapor phase before it is contacted with catalyst 24, and reactor 10 can perform the vaporization without seals 28 and 30 failing and experimental results being compromised.

A. Reactor

Figure 1:
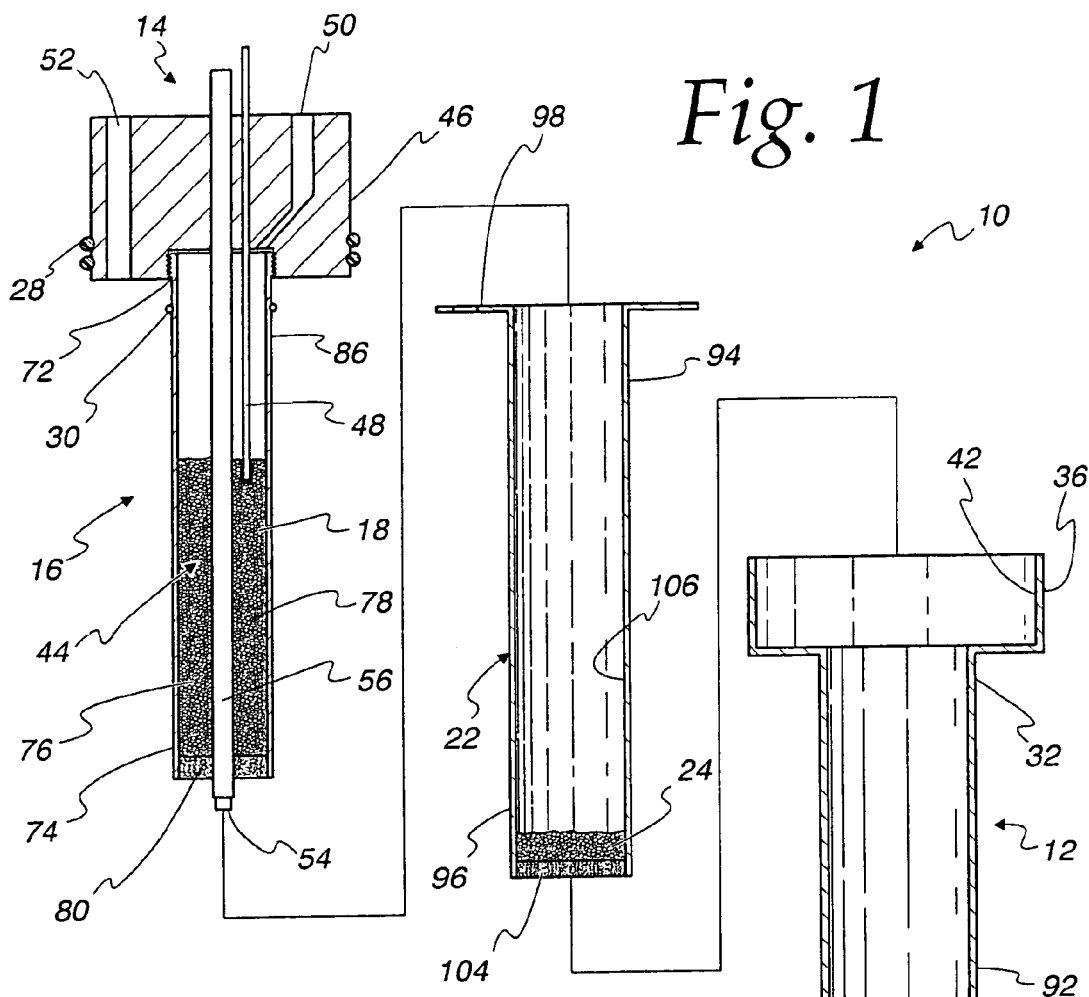
FIG. 1 is an exploded side view of a reactor.

Turning to FIG. 1, reactor 10 includes a housing 12 for housing reactor 10, a header 14 which provides inlets for the feed to housing 12, an insert 16 attached to header 14 which retains an evaporation zone 18 for vaporizing the liquid feed, an evaporator heater 20 (see FIG. 3) for providing the heat necessary to vaporize the liquid feed to form a vapor, and a receptacle 22 which retains a catalyst 24, catalyst 24 forming a reaction zone 26. The vapor is contacted with catalyst 24 and reacted to form a product. A gas feed may also be introduced to reactor 10, mixed with the vapor in the evaporation zone 18, and reacted with the vapor in the presence of catalyst 24 to form the product gas.

The liquid feed may be any liquid component or mixture of liquid components, that is able to be vaporized under predetermined temperatures and pressures and is intended to undergo a reaction that is capable of being catalyzed by catalyst 24. The feed is preferred to be a liquid hydrocarbon mixture. Examples of hydrocarbon intended for the use in reactor 10 are aromatic, aliphatic, and naphthene compounds having six or more carbon atoms, preferably six to nine carbon atoms. Examples of intended feed components are benzene, toluene, xylenes, ethyl benzenes, cumene, higher alkyl substituted benzenes, cyclohexanes, cyclopentanes, higher alkyl substituted cyclic paraffins, pentanes, hexanes, heptanes, octanes, nonanes, decanes, and higher molecular weight aliphatics and mixtures of the above. Alternatively, the liquid feedstock may be or may contain one or more components having hydrogen, carbon, and another element such as oxygen, chlorine, sulfur, nitrogen, and the like.

A gas feed is not necessary for the use of reactor 10, but is included in the discussions below merely to exemplify reactions involving a gas feed as well as a liquid feed. The gas feed may be any gas that can activate or reactivate surface reactive sites or undergo reaction that is capable of being catalyzed by catalyst 24 and could be an organic or inorganic gas. Examples of gas feeds are hydrogen gas, oxygen gas or light hydrocarbons in the gas phase such as methane or ethane. Alternatively, the gas feed could be an inert gas, such as Nitrogen, to act as a carrier for the vaporized liquid feed but not intended to react in reaction zone 26. The feed to the reactor of the present invention may be one or more gas phase feeds, one or more liquid phase feeds, or a combination of one or more gas phase feeds and one or more liquid phase feeds.

Both the liquid feed and the gas feed are introduced to reactor 10 in measured amounts, and with known compositions so that the amount of each component being introduced to reactor 10 is known. The known amount of each component entering reactor 10 combined with the measured flow rate and the analyzed composition of the product gas is used to determine the activity, feed conversion, major product and byproduct selectivities and yields of catalyst 24 in reactor 10.

A first seal 28 is placed between the header 14 and the housing 12 to provide a barrier between reactor 10 and its environment and a second seal 30 is placed between the insert 16 and receptacle 22 to prevent leaks between the insert 16 and receptacle 22. The removable parts of reactor 10, along with seals 28 and 30, allow for easy assembly and disassembly of reactor 10, as well as allowing individual parts to be replaced if needed. For example, if receptacle 22 becomes damaged, it can be replaced easily with an identical receptacle 22 simply by placing the new receptacle 22 into reactor 10 and engaging seals 28 and 30. Other parts that are not damaged, do not need to be replaced. The ability of housing 12, insert 16 and receptacle 22 to be removed and replaced allows easy assembly of reactor 10, which is beneficial for the experimental setup of a combinatorial array 120.

Dimensions will be provided for the elements of reactor 10, however the inventive reactor 10 of the present invention is not limited to the dimensions described below, which are provided simply for context in the preferred case of a combinatorial-scale reactor to be used in an array. It is conceivable that reactor 10 could be scaled up to a pilot plant or even a commercial scale or scaled down to micro-scale without varying from the generally broad scope of the invention.

1. Housing

As is best shown in FIG. 1, housing 12 includes an inlet end 32 for receiving feeds and an outlet end 34 for products. Housing 12 encases evaporation zone 18 and reaction zone 26. Housing 12 includes a shoulder 36 at inlet end 32 of housing 12, a main section 38 between shoulder 36 and outlet end 34, and a product conduit 40 at the outlet end 34. Product conduit 40 is attached to housing 12 at the outlet end 34 and allows a path for product to be withdrawn from reactor 10. Shoulder 36 includes a surface 42 for seal 28 to engage between housing 12 and header 14. Seal 28 prevents feeds from leaking from reactor 10 into the environment. Seal 28 may be retained by shoulder 36 of housing 12 or it may be retained by header 14 without varying from the scope of the invention.

Seal 28 may be any type capable of forming a reliable, pressure-tight seal between housing 12 and header 14, but it is preferred that seal 28 be of a type that allows quick assembly of reactor 10. An example of an acceptable seal 28 being an elastomeric O-ring, or set of O-rings engaged between housing 12 and header 14. However, typical elastomeric O-ring seals have a maximum temperature limitation for long-term operation of between about 170° C. and 300° C., which is lower than the bubble points of most liquid feeds that will be introduced to reactor 10. For example, boiling points of $C_6$ to $C_9$ hydrocarbons at pressures of between about 400 psig (2860 kPa) and about 500 psig (3351 kPa) range from about 300° C. and about 400° C. Note that the present invention is not limited to operating pressures in the range of 400 psig (2860 kPa) to 500 psig (3351 kPa). Reactor 10 of the present invention could be operated at ambient pressure or in vacuum, or at pressures higher than 500 psig (3351 kPa). The only limitation on operating reactor pressure is a differential pressure limitation on seal 28.

Because of bubble or boiling points that are higher than maximum seal limitations, many liquid feeds cannot be vaporized upstream of reactor 10, because their elevated temperatures would compromise the integrity of seals 28 and 30. To solve this problem, an evaporator 44 is placed within reactor 10, downstream of seal 28 so that the maximum temperature limitation is not reached at seal 28. It is also desirable to keep seals 28 and 30 in a cool zone that is separate from the heated evaporation zone 18.

Housing 12 and shoulder 36 are preferably cylindrical in shape, but may be of another geometric shape. For ease of discussion, housing 12 and shoulder 36 will each be described as a cylinder having a length and a diameter, but it must be emphasized that the invention is not limited to a cylindrical shape having the size described herein. Other shapes and sizes of housing 12 could also be successfully employed. For the purpose of combinatorial use, reactor 10 is preferred to be small and easy to manipulate so that an array 120 of multiple reactors 10 can be assembled easily without the use of bulky parts.

In one embodiment, main section 38 of housing 12 may have a length of between about 13 cm and 14 cm and an inner diameter of between about 0.4 cm and about 0.5 cm. Shoulder 36 may have a length of about 1.0 cm and a diameter of between about 0.8 cm and about 1.0 cm. Product conduit 40 may have an inner diameter of less than 1 mm to about 1.5 mm. However, housing 12, shoulder 36 and product conduit 40 are not limited to the above dimensions and could be scaled up or down without varying from the scope of the present invention.

Housing 12 is preferably constructed out of a material that is inert to reaction with the liquid and gas feeds, is resistant to corrosion, can withstand temperatures of from about 10° C. to about 1000° C., and has good heat transfer properties. Examples of suitable materials of construction include metals and their alloys, low grade steel, stainless steels, super-alloys like Incolloy, Inconel and Hastelloy, engineering plastics and high temperature plastics, ceramics such as silicon carbide and silicon nitride, glass, and quartz. A preferred material of construction of housing 12 is 321 stainless steel and a preferred material of construction of shoulder 36 is 316 stainless steel.

2. Header

As shown in FIG. 1, header 14 and insert 16 are connected to each other so that header 14 and insert 16 form a single piece. Header 14 and insert 16 may be connected by any number of methods such as threading, bolting or welding, but it is preferred that they be able to be disengaged from one another so that packing 76 may be changed out if desired.

Header 14 provides fluid to inlet end 32 of housing 12. Header 14 also provides a surface 46 for seal 28 to engage between header 14 and housing 12 at shoulder 36, however seal 28 could engage between housing 12 and insert 16. Header 14 includes an injector 48 for a liquid feed inlet, a gas feed inlet 50, a diluent gas inlet 52 and a guide tube 56 for a thermocouple 54 to measure the temperature within reactor 10. Header 16 is received by housing 12 at inlet end 32.

It is preferred that the cross-section of header 14 be of the same general shape as the cross-section of housing 12 so that header 14 will easily fit within shoulder 36 of housing 12 within predetermined tolerances. It is preferred that header 14 be generally cylindrical, but header 14 could be generally of another geometric shape. For ease of discussion, header 14 will be described as being generally cylindrical with a length and a diameter. Header 14 fits within shoulder 36 of housing 12, engaging with seal 28, so that a portion of header 14 is above shoulder 36 of housing 12.

The length of header 14 is preferably larger than the length of shoulder 36 of housing 12 and the diameter of header 14 is preferably slightly smaller than the diameter of shoulder 36 of housing 12 within tolerance limits so that an adequate seal can be formed between header 14 and housing 12. The diameter of header 14 is also preferred to be large enough so that there is enough area injector 48, gas feed inlet 50, diluent gas inlet 52 and guide tube 56. In one embodiment, header 14 may have a length between about 1.0 cm and about 1.5 cm and a diameter of between about 0.8 cm and about 0.9 cm. However, header 14 is not limited to the above dimensions and could be scaled up or down without varying from the scope of the present invention.

Like housing 12, header 14 is preferably constructed out of a material that is inert to reaction with the liquid and gas feeds, is resistant to corrosion, can withstand temperatures of from about 10° C. to about 1000° C., and has good heat transfer properties. It is preferred that housing 12 and header 14 be made from similar, or identical materials. Examples of suitable materials of construction include metals and their alloys, low grade steel, stainless steels, super-alloys like Incolloy, Inconel and Hastelloy, engineering plastics and high temperature plastics, ceramics such as silicon carbide and silicon nitride, glass, and quartz. A preferred material of construction of header 14 is 316 stainless steel.

Injector 48 passes through inlet end 32 of housing 12 via header 14 and is in fluid communication with the interior of insert 16 so that injector 48 extends substantially into insert 16, and liquid feed is introduced through an orifice 66 of injector 48 into insert 16. Preferably, orifice 66 is located within evaporation zone 18 so that the liquid feed is introduced directly into evaporation zone 18. Preferably, injector 48 is placed so that it is approximately centered radialy within the insert 16. The radial centering allows for uniform distribution of the liquid feed within evaporator 44. Injector 48 is preferably tubular with a small inside diameter and an orifice 66. In one embodiment the diameter of orifice 66 of injector 48 may be about 0.2 mm. The length of injector 48 that is within insert 16 may be about 5 cm.

Gas feed inlet 50 extends through header 14 and is in fluid communication with insert 16 so that a gas feed introduced to the insert 16 enters upstream of a liquid feed introduced to insert 16. Diameters of gas feed inlet 50 may be larger than the diameter of liquid feed inlet. The diameter of gas feed conduit is chosen to accommodate a predetermined flow rate of gas feed. In one embodiment gas feed inlet 50 may have a diameter of less than 1 mm. The length of gas feed inlet 50 is approximately the same as the length of header 14.

Diluent gas inlet 52 extends through header 14 and through a fluid path 68 in reactor 10 so that the diluent gas can bypass catalyst 24 and dilute the product stream and prevent condensation, as discussed below. The diluent gas may be any gas used to dilute the product and suppress the partial pressure of the product or unreacted feed to prevent condensation. It is preferred that the diluent gas be the same gas as the gas feed so that they may be introduced from a common reservoir, but any gas may be used to dilute the product stream. The diameter of diluent gas inlet 52 is chosen to accommodate a predetermined flow rate of the diluent gas. In one embodiment, diluent gas inlet 52 may have an inner diameter less than 1 mm. The length of diluent gas inlet 52 is approximately the same as the length of header 14.

Optional thermocouple 54 is placed within reactor 10 for measuring the temperature within housing 12. Preferably, optional thermocouple 54 measures the temperature within reaction zone 26. In one embodiment, thermocouple 54 is retained by a guide tube 56 in header 14 and extends along the length of insert 16 and passes into receptacle 22 so that a sensor 70 of thermocouple 54 is generally centered within reaction zone 26. However, only the location of sensor 70 effects the invention. Thermocouple 54 may be placed so that it is inserted through the sides of housing 12 and receptacle 22 so that sensor 70 is generally centered within reaction zone 26.

Optional guide tube 56 provides a way for a thermocouple 54 to be easily placed into reactor 10 to measure the temperature within reaction zone 26. The diameter of guide tube 56 depends on the diameter of thermocouple 54. In one embodiment, the inner diameter of guide tube 56 may less than 1 mm.

However, injector 48, gas feed inlet 50, diluent gas inlet 52 and guide tube 56 are not limited by the above dimensions and could be scaled up or down without varying from the scope of the present invention.

Guide tube 56 is preferably constructed out of a material that is inert to reaction with the liquid and gas feeds, is resistant to corrosion, can withstand temperatures of from about 10° C. to about 1000° C., and has good heat transfer properties. It is preferred that guide tube 56 is constructed from similar or identical materials as the housing 12 and header 14. Examples of suitable materials of construction include metals and their alloys, low grade steel, stainless steels, super-alloys like Incollsy, Inconel and Hastelloy, engineering plastics and high temperature plastics, ceramics such as silicon carbide and silicon nitride, glass, and quartz. A preferred material of construction of guide tube 56 is 321 stainless steel.

3. Insert

Header 14 and insert 16 are disengageably connected so that header 14 and insert 16 form a single piece. Header 14 is adjacent to insert 16 so that injector 48 and gas feed inlet 50 are in fluid communication with evaporation zone 18. Header 14 and insert 16 may be connected by any number of methods such as threading or bolting, but it is preferred that they be able to be disengaged from one another so that packing 76 may be changed out if desired.

Header 14 and insert 16 are placed within housing 12 so that seal 28 is engaged between header 14 and housing 12, sealing reactor 10 from its environment and so that insert 16 is within receptacle 22. Insert 16 is preferably removable. Insert 16 includes an inlet end 72 and an outlet end 74. Insert 16 contains packing 76 to form a bed 78 within evaporation zone 18 for vaporizing the liquid feed to form a vapor. Although particulate packing 76 as described is preferred, other evaporation surfaces may be employed instead of a particulate packing 76 (see below).

A fluid permeable member 80 is attached at outlet end 74 of insert 16 to retain packing 76, but still allow fluids, such as the gas feed and the vapor to pass into receptacle 22 to be contacted with catalyst 24. Fluid permeable member 80 is preferably a sintered metal, such as Hastelloy, but could be any material that is permeable to the fluids flowing into reaction zone 26 in receptacle 22 and sufficiently strong to support packing 76. Other possible materials of fluid permeable member 80 include glass, sintered glass, Raney metals, electro-bonded membranes, etched alloy membranes, and fine meshed screens with gaps smaller than the minimum packing size, but large enough to allow the gas feed and vapor to flow adequately.

Figure 4:
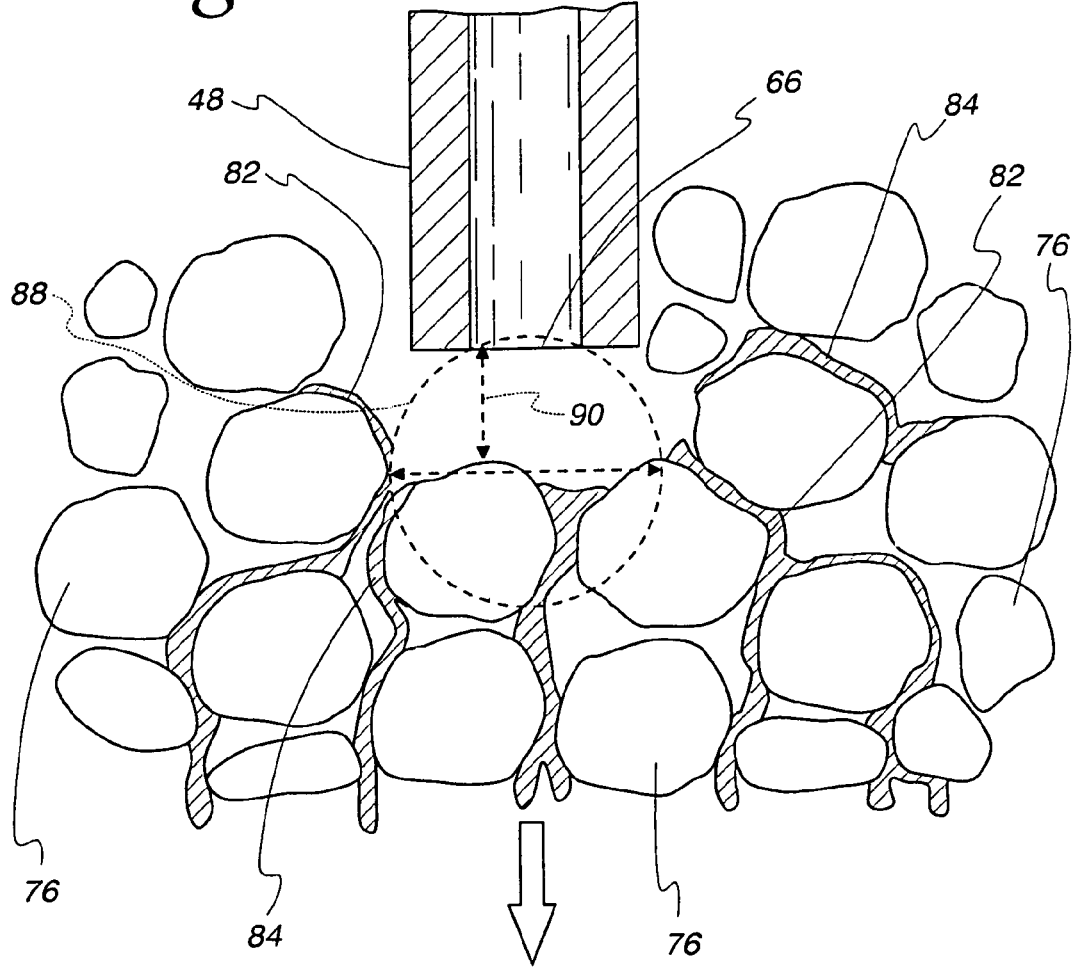
FIG. 4 is a side close up view of the orifice of the injector and the packing.

Packing 76 could be in any form, so long as it interferes with the formation of a droplet (described below) and provides surfaces 82 for the liquid feed to form a thin liquid film 84. Packing 76 may be particulate packing, as shown in FIG. 4, or it may be a prefabricated, structured monolithic packing, or it may be another means to interfere with droplet formation and provide surfaces for the formation of a thin liquid film 84, such as a metal insert placed within evaporation zone 18 near orifice 66. For ease of discussion, packing 76 is described as a particulate packing having a diameter.

Thin liquid film 84 allows efficient evaporation of the liquid feed when heat is provided by an evaporator heater 20. Packing 76 is preferably inert to the gas feed and the liquid feed and may be any inert packing material, such as alumina, and preferably microporous alumina. Packing 76 may be of a uniform size with the same diameter for each particle, or of a random size with minimum and maximum particle diameters. The minimum diameter of packing 76 is preferably larger than the diameter of orifice 66 of injector 48 so that packing 76 does not clog injector 48, and the maximum diameter of packing 76 should be no larger than about 10% of the inner diameter of insert 16 to prevent the formation of wall flow along interior surface of insert 16. In one embodiment, the diameter of packing 76 may be between about 0.21 mm and about 0.42 mm.

Insert 16 is preferably of the same general shape as housing 12 so that it will fit easily within housing 12. Insert 16 is preferably cylindrical in shape, but may be of another geometric shape. For ease of discussion, insert 16 is described as a cylinder having a length and a diameter. In one embodiment, insert 16 may have a length of about 10 cm and a diameter of about 0.3 cm. The diameter of insert 16 is chosen so that insert 16 will fit within receptacle 22 within predetermined tolerances. Insert 16 is not limited to the above dimensions and could be scaled up or down without varying from the scope of the present invention.

Insert 16 is preferably constructed out of a material that is inert to reaction with the liquid and gas feeds, is resistant to corrosion, can withstand temperatures of from about 10° C. to about 1000° C., and has good heat transfer properties. It is preferred that insert 16 be constructed of a similar, or identical material as the housing 12 and header 14. Examples of suitable materials of construction include metals and their alloys, low grade steel, stainless steels, super-alloys like Incolloy, Inconel, Hastelloy, engineering plastics and high temperature plastics, ceramics such as silicon carbide and silicon nitride, glass, and quartz. A preferred material of construction of insert 16 is 321 stainless steel.

Insert 16 also provides a surface 86 for seal 30 to engage between insert 16 and receptacle 22. Seal 30 prevents the feeds from leaking past catalyst 24 and prevents the diluent gas from passing into receptacle 22 and coming into contact with catalyst 24. Seal 30 may be retained by insert 16, header 14 or receptacle 22 without varying from the scope of the invention.

As with seal 28, seal 30 may be of any type capable of forming a reliable, pressure tight seal between insert 16 and receptacle 22, but it is preferred that seal 30 be of a type that allows quick assembly of reactor 10. An example being an elastomeric O-ring, or set of O-rings to engage between insert 16 and receptacle 22. However, most elastomeric O-ring seals have a maximum temperature limitation that is lower than the bubble point of most liquid feeds that will be introduced to reactor 10.

4. Evaporator—Evaporation Zone

Because of bubble points higher than maximum seal limitations, most liquid feeds cannot be vaporized upstream of reactor 10 because their elevated temperatures would compromise the integrity of seals 28 and 30. To solve this problem, an evaporator 44 is placed within reactor 10, downstream of seal 30 so that the maximum temperature limitation is not reached at seal 30.

Integrating an evaporator within reactor 10 has some inherent problems that need to be overcome in order for evaporator 44 to be effective, and provide a vaporized gas stream with a constant and uniform composition. One of these problems is non-uniform mixing of a gas feed and liquid feed, and another is non-uniform vaporization of a liquid feed. If the composition of the gas entering reaction zone 26 is not uniform, it will create unreliable results. With one main purpose of reactor 10 being the evaluation of catalysts, unreliable results would yield unreliable data on catalyst 24 for the reaction in question.

One problem associated with evaporators in general is non-uniform mixing of a liquid feed and a gas feed. One way non-uniform mixing occurs is when both a gas and a liquid are introduced to an evaporator through a common inlet. The combined feed of liquid and gas causes alternating regions of gas entrainment and liquid pulsation being introduced to an evaporator, and therefore regions of low concentration of the vaporized species followed by regions of high concentration of the vaporized species being sent to a reactor bed.

Another problem associated with evaporators in general is non-uniform vaporization which occurs mainly because of a non-uniform flow of liquid into an evaporator. In the case of slower moving flow, a liquid issuing from an orifice into an evaporator can form droplets that detach at a regular periodicity because of the fluid dynamics of the liquid. The periodic formation and detachment of droplets leads to non-uniform vaporization within the evaporator.

A stream of liquid issuing out of an orifice can become unstable due to capillarity. This instability results in the formation of drops the size of which can be accurately predicted by linear stability analysis. The character of the liquid breakup at the orifice is primarily controlled by the Weber number, We:

$$We = \frac{\rho D U^2}{\sigma}$$

where D is the diameter of the orifice, U is the average liquid velocity, $\rho$ is the liquid density and $\sigma$ is the surface tension. The Weber number expresses the balance between external kinetic force and surface force, wherein the external force on the droplet is defined by:

$$F_D = \frac{\rho U^2}{2} \cdot \frac{\pi D^2}{4}$$

and the surface force of the droplet is defined by:

$$F_S = \pi D \sigma$$

The free interface of the droplet is stable when $F_D < F_S$ or:

$$\frac{\rho U^2}{2} \cdot \frac{\pi D^2}{4} < \pi D \sigma \quad We = \frac{\rho D U^2}{\sigma} < 8$$

When the Weber number is less than 8, a stable interface is created and uniform axi-symetric droplets form at the orifice. In the case of reactor 10, liquid is introduced to evaporator 44 at low liquid flow rates, which result in low liquid velocities. For reactor 10, it is not uncommon to have Weber numbers that are much less than one. At very low Weber numbers the droplets approach static equilibrium conditions, and the droplet diameter can be very accurately predicted using the Young-LaPlace equation:

$$\left(\frac{\pi s^3}{6}\right) g (\rho_L - \rho_G) = \pi D \sigma$$

where s is the predicted diameter of the droplet, g is the acceleration of gravity, $\rho_L$ is the density of the liquid, $\rho_G$ is the density of the gas, D is the diameter of the orifice and $\sigma$ is the surface tension of the liquid.

The droplet volume and liquid flow rate allow the estimation of droplet detachment times, in the case of reactor 10 of between about 4 and about 6 seconds. The periodic detachment of droplets leads to severe malfunctioning patterns of vapor concentrations associated with non-uniform vaporization of the droplets.

In the inventive evaporator 44 of the present invention, the problem of non-uniform mixing is solved by feeding the liquid feed and gas feed at different locations within insert 16 so that mixing occurs between the gas feed and liquid feed in evaporation zone 18, not in injector 48. Liquid feed enters insert 16 through orifice 66 of injector 48, where orifice 66 is a substantial distance down the length of insert 16, while gas feed enters insert 16 near inlet end 72 of insert 16. Preferably, orifice 66 is located within evaporation zone 18.

To prevent periodic droplet formation and detachment, and thereby solve the problem of non-uniform vaporization, at least one evaporation surface, such as surfaces 82 of packing 76, is placed within the inventive evaporator 44 of the present invention relative to orifice 66 of injector 48 to interfere with the formation of droplets.

Evaporation surfaces other than those on packing 76 as described may be successfully employed in the present invention. Examples of such evaporation surfaces include, but are not limited to, plates, a porous monolith, a cone, and the like. The selected evaporation surface is positioned to prevent the formation of a droplet at orifice 66 of injector 48. The description herein will exemplify the preferred embodiment where the evaporation surfaces are surfaces 82 of packing 76, however, one of ordinary skill in the art would readily understand the invention as employing other suitable evaporation surfaces.

Bed 78 provides an evaporation zone 18 necessary to effectively vaporize the liquid feed. Evaporation zone 18 is encased within housing 12. FIG. 4 shows a close up view of injector 48 and packing 76 at the point where the liquid feed is injected into bed 78. Injector 48 includes orifice 66 with a diameter D at its terminal end. Liquid feed flows through injector 48 at a average liquid flow rate, U, that would result in the periodic formation of a droplet 88 with a diameter, s, as shown in FIG. 4, where s is determined by the Young-LaPlace equation. Packing 76 is placed in close proximity to orifice 66, defining a gap 90 between orifice 66 and packing 76. It has been hypothesized that if gap 90 is sufficiently smaller than the predicted diameter s of droplet 88, then packing 76 will interfere with the formation of a stable interface and droplet 88 is not allowed to form. Instead, the liquid feed forms a thin liquid film 84 on the surfaces 84 of packing 76 allowing uniform vaporization of the liquid feed. Because of the uniform vaporization, a constant concentration of vapor is contacted by catalyst 24, resulting in accurate results obtained by reactor 10. It is preferred that gap 90 be minimized to be as small as possible without plugging orifice 66 to ensure that packing 76 interferes with the creation of a stable interface of droplet 88.

Unexpectedly, a minimized gap 90 between packing 76 and orifice 66 in inventive evaporator 44 of the present invention is so effective that attempts to reproduce non-uniform vaporization by setting evaporator heater 20 low enough so that the temperature of the liquid feed is below its bubble point until well into bed 78 were unsuccessful. No malfunctioning concentration patterns were created by evaporator 44, despite the attempt to artificially produce them.

In order to ensure adequate flow distribution over packing 76 in bed 78, it is important to use appropriate sizes of packing 76. Diameters of packing 76 should be small enough to avoid a "wall effect" of the liquid flowing along the inner surface of insert 16. Preferably, the maximum diameter of packing 76 should be less then about 10% of the inside diameter of insert 16 to avoid wall flow. However, the minimum diameter of packing 76 should be larger than the diameter of orifice 66 to prevent clogging of orifice 66 by particles of packing 76. In one embodiment, the diameter of packing 76 may be between about 0.21 mm and about 0.42 mm. However, packing 76 is not limited to the above dimensions and could be scaled up or down without varying from the scope of the present invention.

Evaporator 44 of reactor 10 is not limited to use in a reactor. Evaporator 44 itself is novel and inventive and provides an improvement over previous evaporators. The inventive evaporator 44 of the present invention could also be used in another process vessel where it is desirable to vaporize a liquid feed, followed by further processing in a treatment zone within the same process vessel. The process vessel would have both an evaporation zone and a treatment zone, with the evaporation zone including the inventive evaporator 44. In the case of the present invention, reactor 10 is the process vessel and reaction zone 26 is the treatment zone of the vapor.

5. Evaporator Heater

Figure 3:
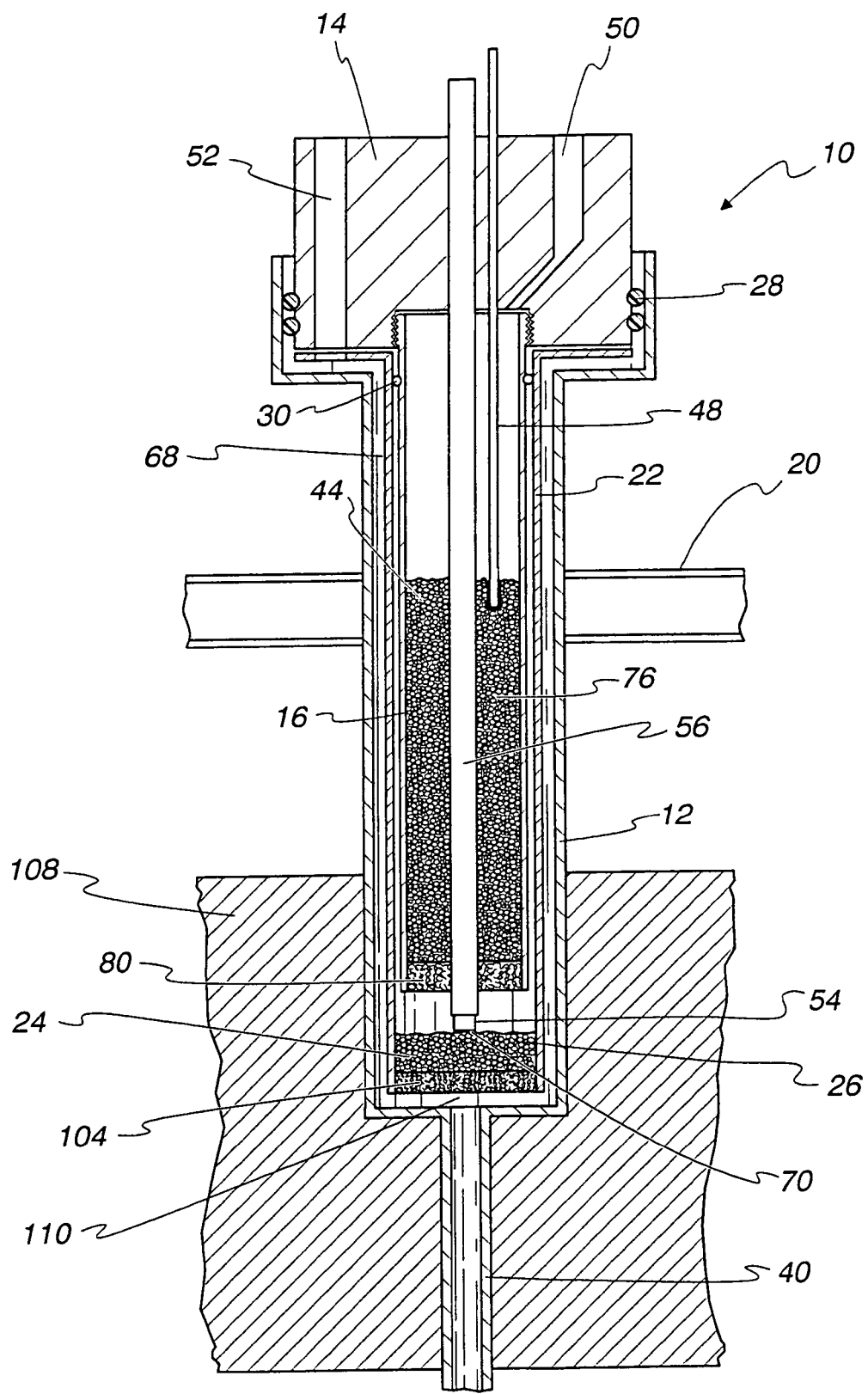
FIG. 3 is a cross-sectional side view of an assembled reactor.

Evaporator heater 20 provides the necessary energy to vaporize liquid feed within bed 78. Evaporator heater 20 is associated with a portion of reactor 10. Preferably, evaporator heater 20 is associated primarily with evaporation zone 18 at the point where the liquid feed is injected into bed 78 as shown in FIG. 3, although other locations may be successful as well. The duty of evaporator heater 20 is preferably provided by electrical resistive heating adjacent to housing 12. Evaporator heater 20 could be a heater block with a thickness larger then the diameter of housing 12 so that evaporator heater 20 is placed around housing 12 housing 12. However, evaporator heater 20 could be any other type of heater, such as one utilizing a heat transfer fluid, and would not vary from the scope of the invention.

Evaporator heater 20 is set at a temperature sufficient to vaporize the liquid feed within evaporation zone 18, forming a vapor. Preferably, the temperature of the liquid feed at orifice 66 is below its bubble point, and evaporator heater 20 is set so that the liquid feed is heated to above its bubble point within evaporation zone 18, creating a temperature gradient within evaporation zone 18. Still more preferably, evaporator heater 20 is set so that a temperature gradient is created throughout evaporation zone 18 so that the temperature of the vapor is heated to a predetermined reaction temperature within evaporation zone 18 before the vapor enters reaction zone 26.

In one embodiment, the thickness of evaporator heater 20 may be about 8 mm. However, evaporator heater 20 is not limited to the above dimensions and could be scaled up or down without varying from the scope of the present invention.

6. Receptacle

Figure 2:
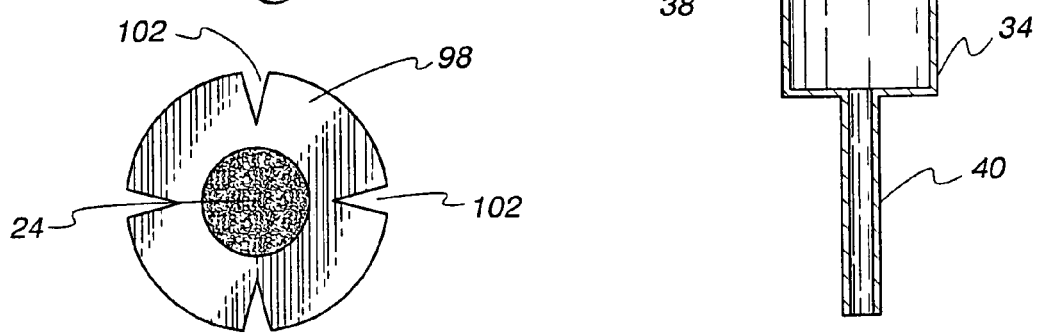
FIG. 2 is a top view of a insert.

Referring to FIG. 3, receptacle 22 is placed within housing 12, and insert 16 is placed within receptacle 22 in a nested configuration so that seal 28 is engaged between header 14 and shoulder 36 of housing 12 and seal 30 is engaged between insert 16 and receptacle 22. Receptacle 22 is preferably removable. Receptacle 22 includes an inlet end 94 and an outlet end 96. A flange 98 is attached to inlet end 94. Flange 98 of receptacle 22 includes cut-out sections 102 (See FIG. 2) to allow a diluent gas to pass through. The diluent gas passes through cut-out sections 102 in flange 98 and into a fluid path 68 formed between receptacle 22 and main section 38 of housing 12.

Receptacle 22 retains catalyst 24, within reaction zone 26. It is within reaction zone 26 that the gas feed and the vapor are contacted, at reaction conditions, with catalyst 24, where they are reacted to form a product. A fluid permeable member 104 is attached at outlet end of receptacle 22 to retain catalyst 24, but allow fluids, such as unreacted feeds and product gas, to pass out of receptacle 22 and exit reactor 10 out of product conduit 40. Fluid permeable member 104 is preferably a sintered metal, such as Hastelloy, but could be any material that is permeable to the fluids passing out of receptacle 22 and sufficiently strong to support catalyst 24. Other possible materials of fluid permeable member 104 include glass, sintered glass, Raney metals, electro-bonded membranes, etched alloy membranes, and fine meshed screens with gaps that are smaller than the size of catalyst 24, but large enough to allow the unreacted feeds and product gas to flow adequately.

Catalyst 24 is selected to provide active sites for the desired reaction. Catalyst 24 may be any material or mixture of materials that possibly catalyze the desired reaction, but preferably catalyst 24 is a zeolite or some other type of catalyst that can be synthesized by combinatorial methods. In one embodiment, an effective mass of catalyst 24 placed within receptacle 22 of reactor 10 may range from about 1 mg to about 1 gram. However, catalyst 24 is not limited to the above masses, and more or less catalyst 24 could be added to reactor 10 without varying from the scope of the present invention.

Reaction zone 26 is flanked by fluid permeable members 80 and 104 upstream and downstream of catalyst 24 and by inner surface 106 of receptacle 22 on the side so that catalyst 24 remains within reaction zone 26. Reaction zone 26 has the same diameter as the inside diameter of receptacle 22. In one embodiment, reaction zone 26 may have a height of between about 1.0 cm and about 1.5 cm.

Receptacle 22 is preferably of the same general shape as housing 12 and insert 16 so that receptacle 22 may easily fit between housing 12 and insert 16 within predetermined tolerances. Receptacle 22 is preferably cylindrical in shape, but may be of another geometric shape. For ease of discussion, receptacle 22 is described as a cylinder having a length and a diameter. The length of receptacle 22 is approximately the same as the length of main section 38 of housing 12. The lengths of insert 16 and receptacle 22 are chosen so that reaction zone 26 has its desired height. The diameter of receptacle 22 is chosen so that fluid path 68 is provided between receptacle 22 and housing 12 to allow the diluent gas to bypass reaction zone 26 as shown in FIG. 3. Fluid path 68 may also be formed by channels or groves in receptacle 22 or housing 12 to allow the diluent gas to bypass reaction zone 26. In one embodiment, receptacle 22 may have a length of between about 10 cm and about 14 cm and a diameter of between about 0.4 cm and about 0.5 cm.

The diameter of flange 98 of receptacle 22 is preferred to be approximately the same as the diameter of shoulder 36 of housing 12. In one embodiment, the diameter of flange 98 of receptacle 22 may be about 0.8 cm.

Receptacle 22 and reaction zone 26 are not limited to the above dimensions and could be scaled up or down without varying from the scope of the present invention.

Receptacle 22 is preferably constructed out of a material that is inert to reaction with the liquid and gas feeds, is resistant to corrosion, can withstand temperatures of from about 10° C. to about 1000° C., and has good heat transfer properties. It is preferred that receptacle 22 be constructed of a similar, or identical material as housing 12 and insert 16. Examples of suitable materials of construction include metals and their alloys, low grade steel, stainless steels, superalloys like Incolloy, Inconel, Hastelloy, engineering plastics and high temperature plastics, ceramics such as silicon carbide and silicon nitride, glass, and quartz. A preferred material of construction of receptacle 22 is 321 stainless steel.

7. Reaction Heater

A reaction heater 108 is placed adjacent to housing 12 so that it is associated primarily with reaction zone 26 and so that all of reaction zone 26 is surrounded by reaction heater 108. Reaction heater 108 provides heat for reaction zone 26 so that catalyst 24 and reaction zone 26 can be maintained at a controlled constant temperature. Reaction heater 108 can be any type of heater to provide the heat needed for reaction zone 26, such as an aluminum-bronze oven using electrical resistive heating.

As shown in FIG. 3, reaction heater 108 is placed around outlet end of housing 12 so that all of reaction zone 26 is within the oven. In one embodiment, reaction heater 108 may have a thickness of about 9 cm and the length of reactor 10 that is within reaction heater 108 may be between about 4 cm and about 6 cm. However, reaction heater 108 is not limited to the above dimensions and could be scaled up or down without varying from the scope of the present invention.

Preferably, the length of reactor 10 that is between evaporator heater 20 and reaction heater 108 is sufficient so that the temperature at packing 76 is substantially independent of the temperature at catalyst 24. The temperature of the liquid feed at orifice 66 of injector 48 should not be affected by how reaction heater 108 is set, and the temperature within reaction zone 26 should not be affected by how evaporator heater 20 is set. In one embodiment, the length of reactor 10 between evaporator heater 20 and reaction heater 108 may be between about 2.5 cm and about 8 cm, but reactor 10 is not limited to this dimension and could be scaled up or down without varying from the scope of the present invention.

8. Diluent Gas and Diluent Zone

Some reaction mixtures of reactor 10 include a liquid feed or a product that has a high dew point. This creates a problem for a product mixture exiting reactor 10 through outlet end after leaving reaction heater 108 because the temperature of the reaction mixture decreases to below the mixture's dew point, causing liquid feed or product to condense out of the gas phase. For some products, not only is the dew point high, but so is a freezing point, so that not only does the product condense out of the gas phase, but it also forms a solid, or plates along product conduit 40. Condensing or plating of product causes two problems. First, it can block or obstruct flow through product conduit 40, and second, it alters the gas phase composition of the product stream. Because it is the gas phase composition that is measured by analyzing downstream of reactor 10, condensation or plating can adversely impact experimental results determined by reactor 10.

It has been verified that the addition of a diluent gas to reactor 10 allows for a reduction in pressure for analysis of product, while preventing the condensation and plating of product. As shown in FIG. 3, diluent gas is introduced through diluent gas inlet 52 of header 14. The diluent gas then passes through cut-out sections 102 in flange 98 of receptacle 22 where it flows into fluid path 68 between receptacle 22 and main section 38 of housing 12 so that the diluent gas bypasses catalyst 24. Fluid path 68 is in fluid communication with diluent gas inlet 52 and diluent gas mixing zone 110. Fluid path 68 may be formed due to a difference in diameter between housing 12 and receptacle 22, as shown in FIG. 3, or housing 12 and receptacle 22 may have a small tolerance between them and fluid path 68 may be formed by grooves or channels in either housing 12 or receptacle 22. Grooves or channels (not shown) may also provide for more efficient heat transfer between the diluent gas and evaporation zone 18 and reaction zone 26.

The diluent gas dilutes product and unreacted feeds in mixing zone 110 downstream of reaction zone 26 and fluid permeable member 104 of receptacle 22 near outlet 34 of housing 12. The addition of diluent gas dilutes the product stream in mixing zone 110, lowering the concentration and partial pressure of trace undesirable by-products in the reactor effluent, thus preventing condensation and/or plating and subsequent equipment fouling.

The diluent gas may be mixed with the product stream at any point downstream of reaction zone 26, but it is preferred that it be mixed before product conduit 40 exits reaction heater 108 so that there is no possibility of condensation or plating of product.

The diluent gas may be any gas capable of mixing with the product stream. It is preferred that the diluent gas be the same as the gas feed so that both the gas feed and the diluent gas may be introduced to reactor 10 from a common gas reservoir. Like the liquid feed and the gas feed, diluent gas is introduced to reactor 10 in a measured amount and with a known composition so that the amount of each component being mixed with the product gas is known.

9. Sampling and Analyzing

Reactor 10 is used to evaluate catalysts by determining their activity and selectivity. To accomplish this, at least a portion of the product gases flowing through product conduit 40 is analyzed by an analyzer 112 to determine its chemical composition. In one embodiment, a portion of the product is sampled prior to analyzation by analyzer 112. The flow rate of product in product conduit 40 is also measured so that the amount of each species exiting reactor 10 can be determined. Analyzer 112 can use any method to determine each product gasses composition, but preferably uses one of the following analytic techniques; spectroscopy, spectrometry, chromatography, nuclear magnetic resonance, or a combination thereof.

10. Alternative Embodiment with Cooler

Figure 5:
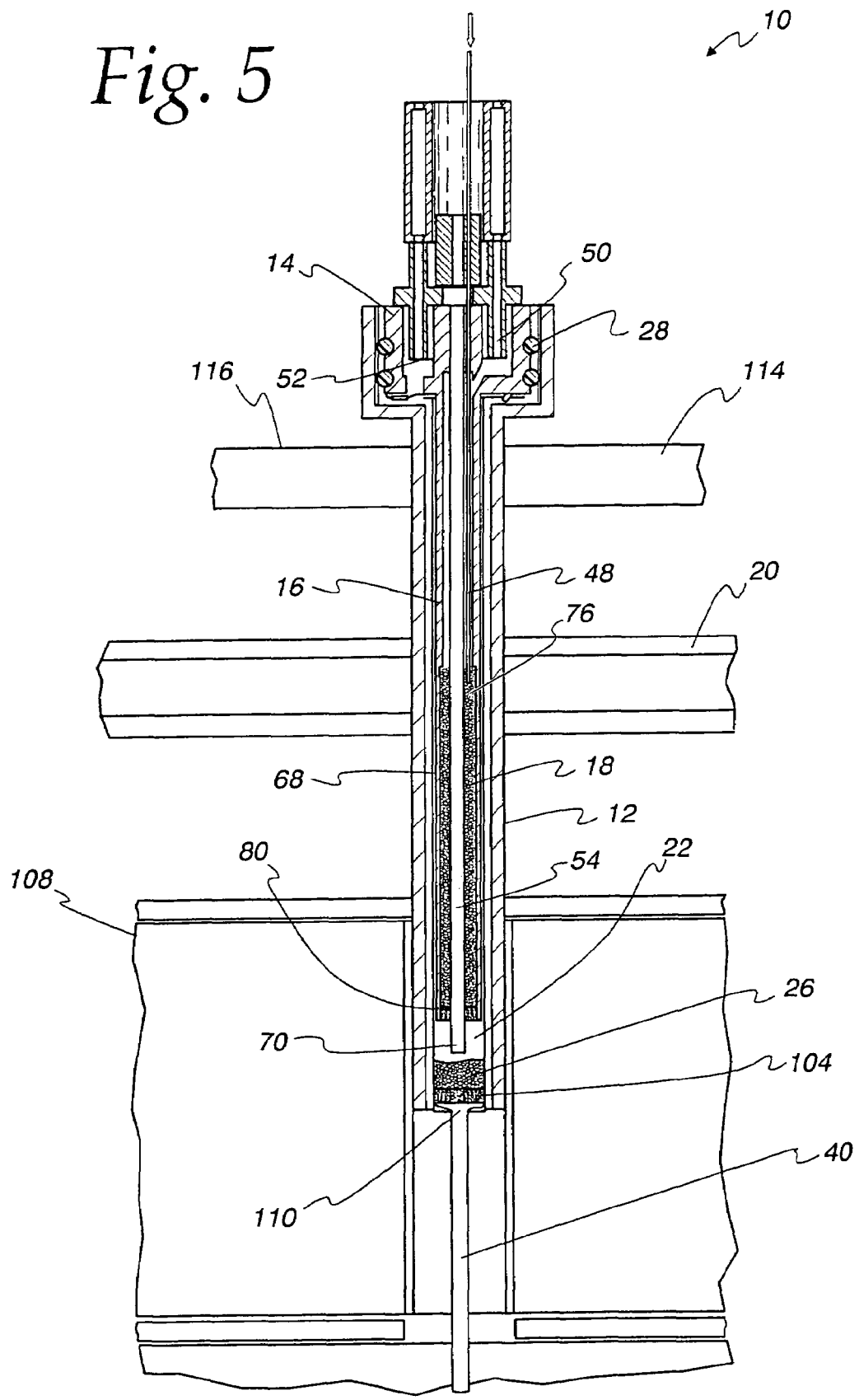
FIG. 5 is a side view of an alternative assembled reactor.

Seals 28 and 30 and both have a maximum temperature limitation that is lower than the bubble point of many liquid feeds that will be introduced to reactor 10. In an alternative embodiment of reactor 10, shown in FIG. 5, a cooler 114 is added to maintain a temperature at seals 28 and 30 to ensure that seals 28 and 30 are not compromised. Cooler 114 is placed adjacent to housing 12 between evaporator heater 20 and header 14, preferably so that cooler 114 is adjacent to both seals 28 and 30. Cooler 114 is set so that the temperature of seals 28 and 30 is below their maximum temperature limitation, ensuring that seals 28 and 30 are not compromised.

Cooler 114 may be of any type capable of removing the heat necessary to maintain seal temperatures below the maximum temperature limitation, but it is preferred that cooler be a plate heat exchanger cooled with water flowing through a conduit within plate 116. Plate 116 of cooler 114 may be made of any heat conducting material, but aluminum is preferred. In one embodiment the thickness of plate 116 of cooler 114 may be about 1 cm and the diameter of the cooling water conduit (not shown) within plate 116 may be about 0.0625 inches. However, cooler 114 is not limited to the above dimensions and could be scaled up or down without varying from the scope of the present invention.

B. Process of Evaporating and Reacting in a Reactor

The process by which reactor 10 vaporizes a liquid feed and reacts the resulting vapor in the presence of catalyst 24 includes the steps of providing packing 76 in evaporation zone 18, providing catalyst 24 in reaction zone 26, introducing a liquid feed to evaporation zone 18, heating and vaporizing the liquid feed within evaporation zone 18 to form a vapor, flowing the vapor into reaction zone 26, and contacting, at predetermined reaction conditions, the vapor with catalyst 24 to form a product. In some cases a gas feed may also be introduced to reactor 10 so that both the gas feed and the vapor are contacted with catalyst 24 in reaction zone 26 to react and form a product.

The liquid feed may be any liquid component or mixture of liquid components, that is able to be vaporized under a predetermined range of temperatures and pressures and may undergo a reaction that may be capable of being catalyzed by catalyst 24. The liquid feed is preferred to be a liquid hydrocarbon. Examples of hydrocarbon intended for the use in reactor 10 are aromatic, aliphatic, and naphthene compounds having six or more carbon atoms, preferably six to nine carbon atoms. Examples of intended feed components are benzene, toluene, xylenes, ethyl benzenes, cumene, higher alkyl substituted benzenes, cyclohexanes, cyclopentanes, higher alkyl substituted cyclic paraffins, pentane, hexanes, heptanes, octanes, nonanes, decanes, and higher molecular weight aliphatics and mixtures of the above. Alternatively, the liquid feedstock may be or may contain one or more components having hydrogen, carbon, and another element such as oxygen, chlorine, sulfur, nitrogen, and the like.

It is preferred that the chemical composition of the liquid feed be known and that the liquid feed be introduced to reactor 10 in a measured amount so that calculations can be performed to determine characteristics of catalysts 24 such as activity, feed conversion, major product and byproduct selectivities and yields.

The gas feed may be any gas that may undergo a reaction that is capable of being catalyzed by catalyst 24, or that may provide a stabilizing effect on the catalyst, and could be an organic or inorganic gas. Examples of gas feeds are hydrogen gas, oxygen gas, nitrogen gas or light hydrocarbons in the gas phase such as methane or ethane. It is preferred that the chemical composition and flow rate of the gas feed into reactor 10 feed be known so that calculations can be performed to determine an activity and selectivity for catalyst 24 as described below.

In one process, catalyst receptacle 22 is placed containing catalyst 24 for reacting vaporized feed within housing 12 where receptacle 22 is positioned within reactor 10 so that catalyst 24 is within reaction zone 26, insert 16 is placed containing packing 76 having surfaces 82 for evaporating feed where insert 16 is positioned within receptacle 22 so that packing 76 is within evaporation zone 18, the liquid feed is injected into evaporation zone 18 through injector 48 in a measured amount, where it passes through header 14 and into insert 16. Next, liquid feed is injected through orifice 66 in injector 48 into bed 78 formed by packing 76, and forms a thin liquid film 84 on the surfaces 82 of packing 76.

After the liquid feed is injected into bed 78 and forms thin liquid film 84, the liquid feed is heated by evaporator heater 20 which is situated so that the liquid feed is heated at or near orifice 66. Evaporator heater 20 is set at a temperature sufficient to vaporize the liquid feed within evaporation zone 18, forming a vapor. Preferably, the temperature of the liquid feed at orifice 66 is below its bubble point, and evaporator heater 20 is set so that the liquid feed is heated to above its bubble point within evaporation zone 18, creating a temperature gradient within evaporation zone 18. Still more preferably, evaporator heater 20 is set so that a temperature gradient is created throughout evaporation zone 18 so that the temperature of the vapor is heated to a predetermined reaction temperature within evaporation zone 18 before the vapor flows into reaction zone 26.

Packing 76 is provided and placed in insert 16 so that there is a gap 90 defined between orifice 66 and packing 76 that is sufficiently small to interfere with the formation of a droplet on injector 48 at orifice 66. Instead of forming a liquid droplet, the liquid feed forms a thin liquid film 84 on surfaces 82 of packing 76 which is easily vaporized. Heat provided by evaporator heater 20 vaporizes the liquid feed within bed 78 before it enters reaction zone 26 to contact catalyst 24 and react. After being heated and vaporized, the resulting vapor flows through the remainder of evaporation zone 18 and passes through fluid permeable member 80 and into reaction zone 26.

If a gas feed is to be introduced to reactor 10, it is introduced through header 14 in a measured amount and enters insert 16 at some point upstream of orifice 66. The gas feed is then mixed with the vapor in evaporation zone 18 and acts as a carrier gas for the vapor as they pass down the remainder of bed 78, through fluid permeable member 80 and into reaction zone 26.

After entering reaction zone 26, the vaporized hydrocarbon feed and the gas feed, if present, as well as catalyst 24 are heated by reaction heater 108 to a predetermined reaction temperature. Reaction heater 108 provides the heat requirement, to maintain a constant, predetermined and controlled temperature in reaction zone 26. To control the temperature of reaction zone 26, the temperature of reaction zone 26 is constantly measured by thermocouple 54. This measured temperature is then used to control the setting of reaction heater 108. For example, if the temperature measured by thermocouple 54 is too high, the actual temperature is compared with a specified temperature to create an error between the two, and this error is used to lower the heater block set-point.

After passing through fluid permeable member 80 in insert 16 into reaction zone 26, the vaporized hydrocarbon and the gas feed quickly reach the predetermined temperature. The vapor and gas feed are contacted with catalyst 24 and go through at least one reaction to generate a product mixture of a product, byproducts, and unreacted feeds. The product mixture then flows out of reaction zone 26 through fluid permeable member 104 and into product conduit 40, where it is carried away from reactor 10.

A portion of the product mixture is sampled and analyzed by analyzer 112 to determine its chemical composition. The product mixture may be analyzed by any of the following analytic techniques; spectroscopy, chromatography, nuclear magnetic resonance, and combinations thereof.

In an alternate embodiment, reaction heater 108 may provide sufficient heat to also heat the packing 76 in evaporation zone 18. With the heat for the packing 76 being provided by reaction heater 108, a gradient of heat may be established across packing 76. The amount of heat provided to the packing 76 may be controlled by the positioning of reaction heater 108 and the distance between reaction zone 26 and packing 76.

As described above, in some cases it may be desirable to dilute the product mixture with a diluent gas after the product has been formed in reaction zone 26 to suppress the partial pressure of one or more components in the product mixture and prevent condensation into the liquid phase or plating into the solid phase. Preferably, the diluent gas is the same gas as the gas feed so that they may be introduced from a common reservoir. It is preferred that the chemical composition and flow rate of the diluent gas into reactor 10 be known so that calculations can be performed to determine an activity, feed conversion, major product and byproduct selectivities and yields for catalyst 24.

If it is desired, the product mixture is diluted with diluent gas in mixing zone 110 after the product mixture has passed through fluid permeable member 104. The diluent gas may be introduced by any number of methods but it is preferred that the diluent gas be introduced to reactor 10 in a measured amount and bypass reaction zone 26 so that the diluent gas does not come in contact with catalyst 24. Feeding the diluent gas to reactor 10 is desirable so that the inlets for the liquid feed, the gas feed and the diluent gas will all be introduced to the apparatus at the same general location. However, diluent gas could be introduced to product mixture by a different method, such as a separate conduit that is in fluid communication with mixing zone 110 of fluid permeable member 104.

After the diluent gas is introduced to product mixture, it quickly mixes with the product mixture in mixing zone 110 in product conduit 40 to suppress partial pressures of the components of the product mixture and forms a diluted product mixture. At least a portion of the diluted product mixture is sampled and analyzed by 112 as described above.

C. Array of Multiple Reactors

Although reactor 10 by itself is an inventive and novel reactor for vaporizing a liquid feed and reacting the resulting vapor in the presence of catalyst 24, it is when an array 120 of two or more reactors 10 is formed and operated in parallel that the present invention provides the fullest range of utility. An array 120 of reactors 10 operated in parallel allows catalyst 24 to be tested at several different reaction conditions, or a plurality of different catalysts 24 to be compared, or a plurality of feeds or feed compositions to be contacted with catalysts 24, or a combination thereof, so that the activity and selectivity of each catalyst 24 can be calculated for various conditions, so that the most effective catalyst, and the optimal conditions for that catalyst, can be determined for the reaction of interest.

Figure 6:
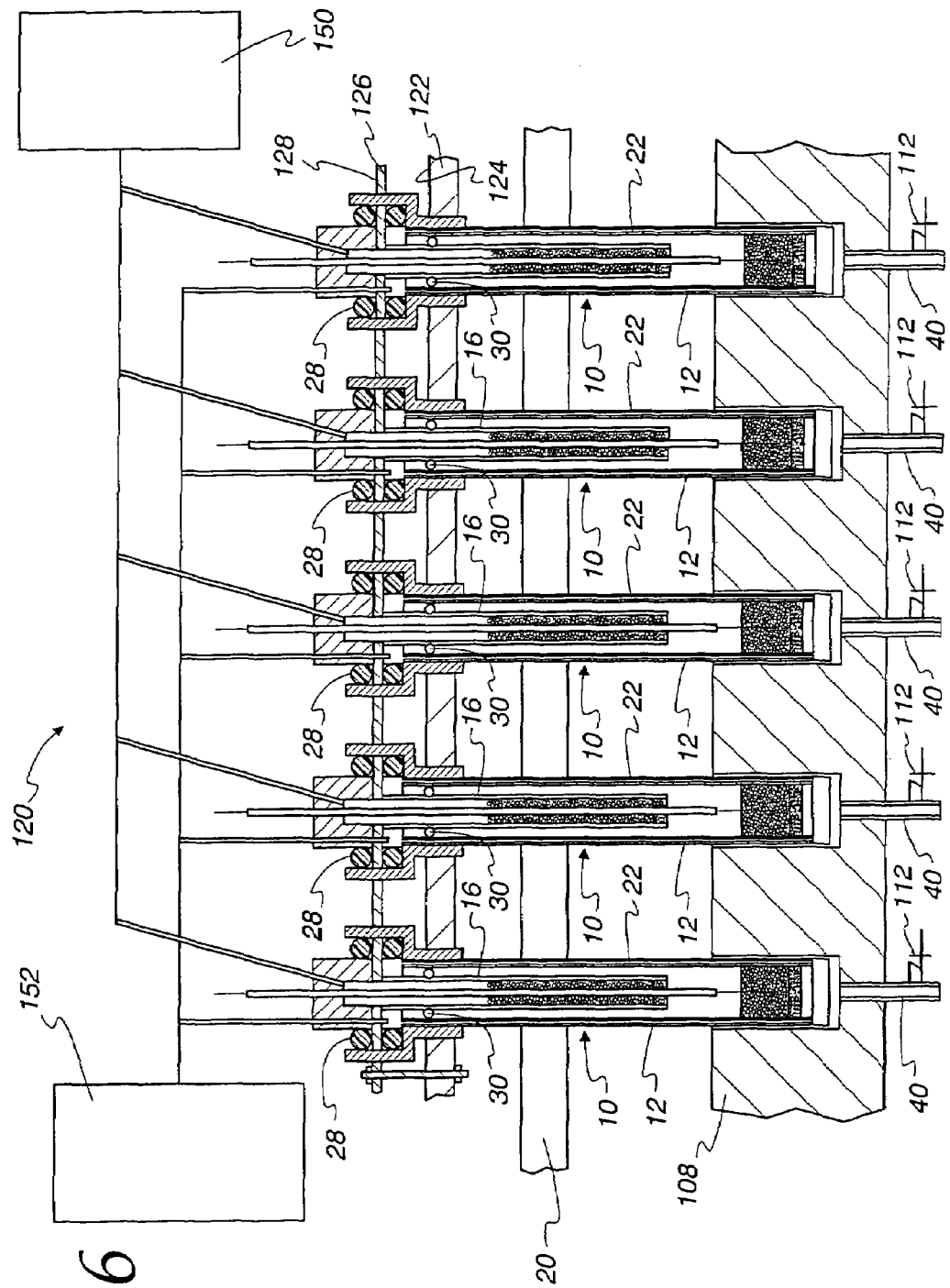
FIG. 6 is a side view of an assembled array.

As shown in FIG. 6, an array 120 of two or more reactors 10 is provided. Each of the reactors 10 of array 120 have all of the elements described above for reactor 10, a housing 12, a header 14, an insert 16 for retaining packing 76 that forms a bed 78 within evaporation zone 18, and a receptacle 22 for retaining catalyst 24 that forms a reaction zone 26. Each reaction zone 26 can consist of the same catalyst 24, and reactors 10 in array 120 can be operated at different reaction conditions, or a plurality of different catalysts 24, or blocks of catalysts 24, can be placed in the reaction zones 26 to compare a plurality of catalysts 24. However, only one evaporator heater 20 is provided to heat the liquid feed at the orifices 66 of the injectors 48 in each reactor 10. Evaporator heater 20 is placed so that it is associated with each of the outside surfaces 92 of each of the housings 12 in array 120.

Reactors 10 in array 120 are intended to perform the same reaction so that common liquid feed, gas feed, and diluent gas is introduced to each reactor 10 in array 120. The liquid feed, gas feed and diluent gas are introduced to reactors 10 simultaneously so that reactors 10 operate in parallel allowing several catalysts 24, or several reaction conditions, to be evaluated simultaneously, greatly decreasing the experimental time requirement associated with testing multiple catalysts 24 at multiple reaction conditions by conventional methods.

1. Each Housing Attached to a Bottom Support Plate

Each housing 12 of array 120 can be a free-standing unit with the features of housing 12 described above, or the housings 12 can be formed from a single tray or block of material. It is preferred that housings 12 be free-standing units so individual housings 12 may be replaced as needed due to damage or change-out. But, it is also preferred that housings 12 be connected to a common bottom support 122 so that the plurality of housings 12 in array 120 can be moved as a single unit, as it is far more convenient to handle an assembly of one unit than to individually manipulate multiple housings 12. Also, robotics, which is frequently used in combinatorial applications, is more readily adapted to manipulating a single tray. It is preferred that each housing 12 in array 120 be constructed of the same material, but it is not necessary. Housings 12 can be constructed of the same materials as housing 12 described above. It is further preferred that inserts 16 and receptacles 22 be constructed of the same material as housings 12.

Bottom support 122 may provide for the connection of any number of individual housings 12. For example, bottom support 122 may connect to 6, 8, 12, 24, 48, 96 or 384 of housings 12. Also, the full capacity of a particular bottom support 122 need not be used. For example, a bottom support 122 designed to hold up to 48 of housings 12 may be used to support only 24. Array 120 is flexible in this respect, because the number of reactors 10 being used by array 120 can be changed simply by adding or taking away a desired number of housings 12 from bottom support 122.

Figure 7:
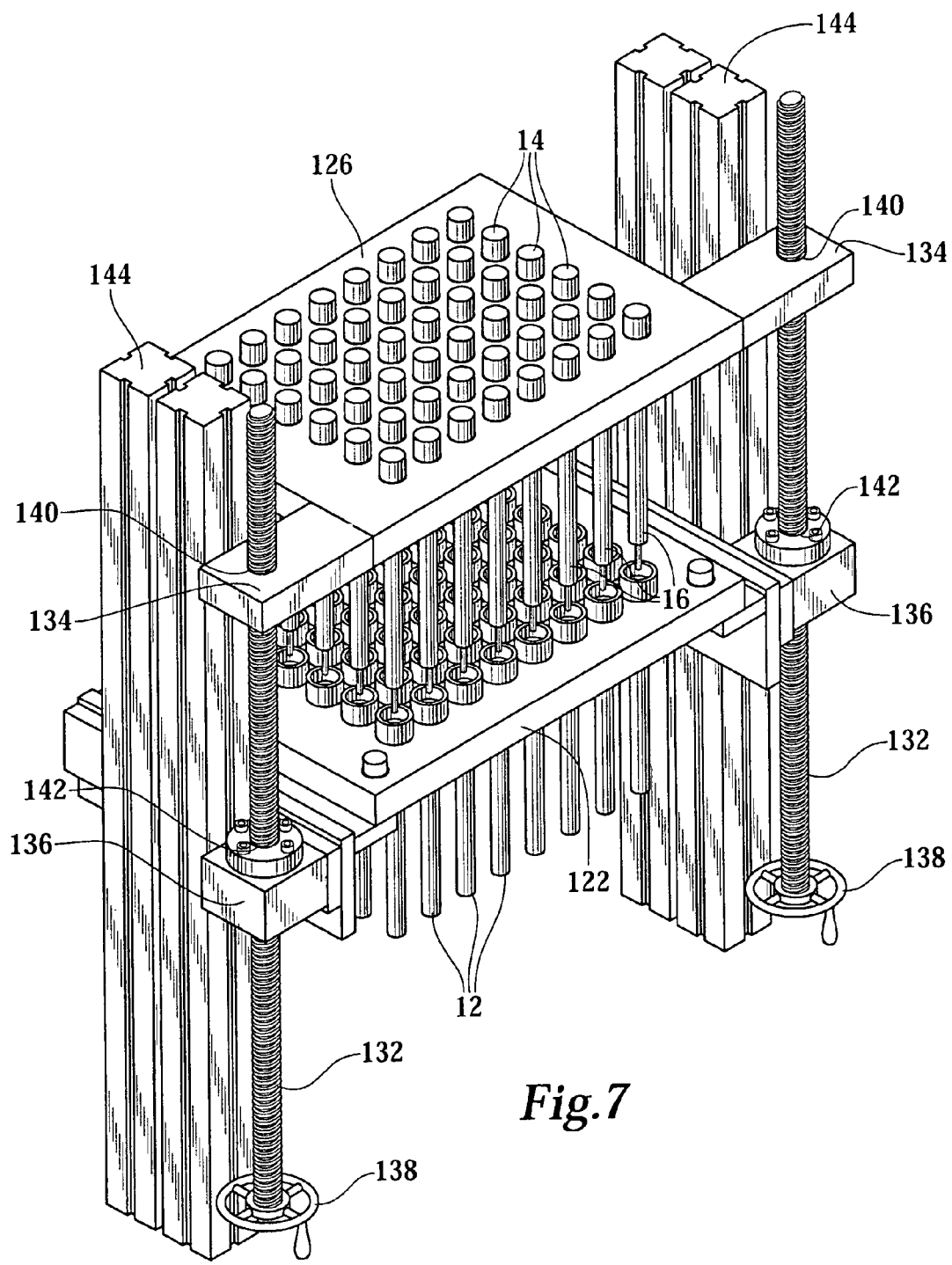
FIG. 7 is a perspective view of the array and the quick connect system.

Bottom support 122 could be any shape or configuration capable of supporting the plurality of housings 12 in a desired, predetermined pattern, but it is preferred that bottom support 122 be a plate with holes for each corresponding housing 12. As shown in FIG. 6 and FIG. 7, the plate of bottom support 122 includes a surface 124 which is generally planar.

As with the housing 12 itself, bottom support 122 may be constructed of a variety of materials including metals and their alloys, low grade steel, and stainless steels, superalloys like Incolloy, Inconel and Hastelloy, engineering plastics and high temperature plastics, ceramics such as silicon carbide and silicon nitride, glass, quartz, Teflon polymer, nylon, and low temperature plastics such as polyethylene, and polypropylene. It is preferred that bottom support 122 be rigid enough to resist twisting from torque so that bottom support 122 remains substantially planar throughout operation of array 120.

Bottom support 122 may allow for the connection of housings 12 in any number of geometrical patterns with the preferred being a grid. It is preferred that bottom support 122 has dimensions similar to the dimensions of commonly used micro titer trays. It is preferred that bottom support 122 be constructed of material that is able to withstand temperatures of from about 10° C. to about 1000° C., and for many catalytic reactions, bottom support 122 may be required to withstand temperatures ranging from about 0° C. to about 1000° C.

2. Each Header Attached to a Top Support Plate

Each housing 12 of array 120 has a corresponding insert 16 and header 14 that has all of the features of insert 16 and header 14 described above. Each of the headers 14 are connected to a top support 126 so that each housing 12 has a corresponding insert 16 placed inside the housing 12 to enclose the plurality of reactors 10 in array 120. Headers 14 are connected to top support 126 so that the plurality of headers 14 and inserts 16 can be moved as a single unit, as it is far more convenient to handle an assembly of one unit than to individually manipulate multiple inserts 16. Also, because housings 12 are connected to bottom support 122 and headers 14 are connected to top support 126, the plurality of headers 14 and inserts 16 can be moved as a single pieces, allowing array 120 to be assembled by one step which simultaneously seals to form array 120.

It is preferred that each header 14 and each insert 16 of array 120 be constructed of the same material, but it is not necessary. Inserts 16 may be constructed from the same materials as header 14 and insert 16 described above. In some applications it may be preferred for headers 14 and inserts 16 to be constructed from the same material, or similar material, as the corresponding housings 12.

Top support 126 may provide for the connection of any number of individual headers 14. For example, top support 126 may connect to 6, 8, 12, 24, 48, 96 or 384 of headers 14. Also, the full capacity of a particular top support 126 need not be used. For example, a top support 126 designed to hold up to 48 of headers 14 may be used to support only 24. Array 120 is flexible in this respect, because the number of reactors 10 being used by array 120 can be changed easily simply by adding or taking away a desired number of headers 14 and inserts 16 from top support 126.

Top support 126 could be any shape or configuration capable of supporting the plurality of inserts 16 in a desired, predetermined pattern, but it is preferred that top support 126 be a plate with holes for each corresponding header 14. As shown in FIG. 6 and FIG. 7, the plate of top support 126 includes a surface 128 which is generally planar.

As with header 14 and insert 16, top support 126 may be constructed of a variety of materials including metals and their alloys, low grade steel, and stainless steels, superalloys like Incolloy, Inconel and Hastelloy, engineering plastics and high temperature plastics, ceramics such as silicon carbide and silicon nitride, glass, quartz, Teflon polymer, nylon, and low temperature plastics such as polyethylene, and polypropylene. It is preferred that top support 126 be rigid enough to resist twisting torque so that top support 126 remains substantially planar throughout operation of array 120.

Top support 126 may allow for the connection of inserts 16 in any number of geometrical patterns with the preferred being a grid. It is preferred that top support 126 has dimensions similar to the dimensions of commonly used micro titer trays. It is preferred that top support 126 be constructed of a material capable of withstanding temperatures from 10° C. to about 1000° C., but a preferred range of temperatures includes temperatures ranging from about 10° C. to about 300° C.

3. Receptacles

Each set of housings 12 and corresponding inserts 16 has a corresponding receptacle 22 for retaining catalyst 24 having the features of the receptacle 22 described above to form a reactor 10 within array 120. Each reactor 10 is assembled in the same manner as described above, except that each reactor 10 is connected to a set of supports 122 and 124 to form array 120.

It is preferred that each receptacle 22 of array 120 be constructed from the same material, but it is not necessary. In some case it may also be preferred for the receptacle 22 to be constructed from the same material, or a similar material, as the housing 12, or the same material, or a similar material, as the insert 16, or both.

4. Quick Connect System Including Quick Sealing

Array 120 of reactors 10 allows for the rapid evaluation of multiple variables simultaneously. For example, each reactor 10 of array 120 can be used to evaluate a different catalyst 24 under the same reaction pressure and temperature and with the same feed compositions, or each reactor 10 can evaluated the same catalyst 24 under varying reaction conditions, such as multiple pressures, temperatures and feed rates and compositions. To fully realize the greatest utility, it is preferred that array 120 include an apparatus that allows for the quick assembly and disassembly of array 120. Seals 28 and 30 aid in this quick-connect because they allow each reactor 10 to be assembled quickly, but still prevent leaks between parts of the reactor and between reactor 10 and its environment. Each seal 28, 30 operates to seal the plurality of reactors 10 simultaneously. Housing support 122 is important because it allows the plurality of housings 12 to be moved as a single piece and insert support 126 is important because it allows the plurality of headers 14 and inserts 16 to be moved as another single piece. However, an apparatus is still needed to raise and lower housing support 122 and insert support 126.

Quick-connect system 130 provides a method to raise and lower supports 122 and 126 while still assuring high precision in the horizontal plane, allowing seals 28 and 30 to seal effectively in each reactor 10. Quick-connect system 130 can be used to raise and lower housing support 122 with insert support 126 remaining stationary, or it can be used to raise and lower insert support 126 with housing support 122 remaining stationary, or each support can have its own quick-connect system and both supports 122 and 126 can be raised and lowered as desired. For ease of discussion, quick-connect system will be described as being used to raise and lower insert support 126 while housing support 122 remains stationary, as shown in FIG. 7, but as discussed above quick-connect system 130 could be used for either support 122 or 126.

One embodiment of quick-connect system 130 includes threaded guide rods 132, guide rings 134, stationary rings 136 and wheels 138. Guide rings 134 are attached to insert support 126 so that they extend away from insert support 126. In FIG. 7, a set of two guide rods 132 are shown, each guide rod 132 having a corresponding guide ring 134, stationary ring 136 and wheel 138. Although two of each of the pieces is shown in FIG. 7, any number could be used without varying from the scope of the present invention.

Each guide rod 132 is threaded so that when it is rotated insert support 126 will be raised or lowered depending on which direction guide rod 132 is rotated. Each guide ring 134 includes a hole 140 that is generally in the center of guide ring 134. It is preferred that hole 140 be generally cylindrical in shape and extend through guide ring 134. Hole 140 is also threaded so that a corresponding threaded guide rod 132 can be placed through hole 140. Guide rod 132 and hole 140 are threaded so that when guide rod 132 is rotated, guide ring 134, and therefore insert support 126, is moved up or down depending on which direction guide rod 132 is rotated.

Each hole 140 includes an inside surface (not shown). It is preferred that the inside surface of hole 140 be generally perpendicular to surface 128 of insert support 126 so that when insert support 126 is raised and lowered surface 128 of insert support 126 remains parallel to surface 124 of housing support 122. This perpendicular raising and lowering of insert support 126 is preferred because it ensures that seals 28 and 30 of each reactor 10 engage simultaneously when each insert 16 is lowered into its corresponding housing 12-receptacle 22 combination as insert support 126 is lowered. If surface 128 of insert support 126 did not remain parallel to surface 124 of housing support 122 not every reactor 10 of array 120 would be sealed. Some of the seals 28 and 30 would engage properly, while other seals 28, 30 would not come into contact with their corresponding housings 12 or receptacles 22 and would fail to properly seal certain reactors 10. Still other seals 28 and 30 could pinch or bind within their corresponding reactors 10, causing a problem when insert support 126 is attempted to be raised because certain inserts 16 would stick within their corresponding housings 12.

Each stationary ring 136 also includes a hole 142 for a corresponding guide rod 132 to pass through. Stationary ring 136 is anchored to a stationary support 144 of array 120 so that it remains stationary while guide rod 132 rotates. Stationary ring 136 keeps guide rod 132 in position while it is rotated so that insert support 126 is raised and lowered instead of guide rod 132. Each hole 142 is threaded, like its counterpart hole 140 in guide ring 134. Each hole 142 includes an inside surface (not shown) that is preferred to be generally perpendicular to the plane of surface 124 of housing support 122 so that surface 124 of housing support 122 and surface 128 of insert support 126 remain parallel throughout operation of quick-connect system 130. Stationary ring 136 could be anchored by any method to any stationary member of array 120, but it is preferred that it be anchored to something near insert support 126 so that guide rod 132 need not be excessively long. In one embodiment, stationary rings 136 are shown to be anchored by anchors 146 to support 144 of housing support 122, as shown in FIG. 7.

Each guide rod 132 has a corresponding wheel 138 which is used to rotate guide rod 132. Each wheel 138 is attached to an end of guide rod 132 and may include a handle 148. If more than one guide rod 132 is used, as shown in FIG. 7, it is preferred that the rotation of guide rods 132 be synchronized to ensure that support 122 or 126 remains in a horizontal plane throughout operation of quick-connect system 130. A means that could accomplish this would be coupling the rods with a belt system (not show) so that both guide rods 132 rotate the same amount at the same time.

Although a quick-connect system 130 with guide rods 132, rings 134, 136 and wheels 138 is described, the present invention is not limited to a quick-connect system 130 with these embodiments. Other means could be used to ensure that support plates 122 and 126 remain in a horizontal plane and remain parallel to each other, such as a precision rail guide system attached to support plates 122 and 126. One of ordinary skill in the art will appreciate the many types of systems that could be used to raise and lower support plates 122 and 126 and still remain within the scope of the present invention.

Guide rods 132, guide rings 134 and stationary rings 136 can be purchased from a supplier so that a predetermined precision can be provided by quick-connect system 130. Examples are catalog numbers S 151101900, S 151201023, S 150600010 and S 159111020 from Rexroth Bosch Group.

5. Common Feed Reservoirs

Array 120 also creates the need for fewer feed reservoirs to store feed liquids and gases to be introduced to the reactors 10 in array 120. Only one liquid feed reservoir 150 is required to introduce liquid feed through injectors 48 associated with each of the reactors 10 of array 120 because each reactor 10 of array 120 is performing the same reaction, with the same liquid feed. Similarly, only one gas feed reservoir 152 is required to introduce feed to the gas feed inlets 50 associated with each header 14. Also, if the diluent gas is the same gas as the gas feed, a third reservoir is unnecessary so that only liquid feed reservoir 150 and a gas feed, reservoir 152 are required for the operation of array 120. However, if a gas other than the gas feed is used as the diluent gas, a third reservoir (not shown) for the diluent gas would be required.

In some cases it may be desirable to introduce the liquid feed, gas feed and diluent gas to reactors 10 in array 120 in measured amounts so that the exact amount of each substance entering each reactor 10 is known. It is desirable to do this because the combination of knowing how much reactant or diluent gas is introduced to each reactor 10 and the composition of the product gas exiting each reactor 10 can be used to calculate the activity, feed conversion, major product and byproduct selectivities and yields for each catalyst 24 in each reactor 10.

6. Sampling and Analyzing

Array 120 is used to evaluate catalysts by determining their activity and selectivity. To accomplish this, at least a portion of each of the product mixtures flowing through each product conduit 40 is sampled and analyzed to determine its composition. Preferably, analyzer 112 uses any one of the following analytic techniques to determine each product gases composition; spectroscopy, spectrometry, chromatography, nuclear magnetic resonance, or a combination thereof.

7. Reaction Heater

As with individual reactor 10, array 120 includes reaction heater 108 shown in FIG. 6. Reaction heater 108 of array 120 provides heat for reaction zones 26 so that catalysts 24 can be kept at a controlled constant temperature. Reaction heater 108 can be any type of heater to provide the heat needed for reaction zones 26, such as an aluminum-bronze oven using electrical resistance heating.

Although FIG. 6 shows a single reaction heater 108 common to all reactors 10 in array 120, in some cases it may be desirable that each reactor 10 in array 120 have its own corresponding reaction heater 108 so that different reactors 10 in array 120 may be kept at different temperatures. Similarly, it may be desirable in some cases to have two or more reaction heaters 108, each reaction heater 108 providing energy for one or more reactors 10 in array 120 so that there are blocks of reactors 10 operating at different reaction temperatures.

D. Process of Evaporating and Reacting in an Array of Reactors

The process of vaporizing liquid feed and reacting the resulting vapor in the presence of catalyst 24 within each reactor 10 of array 120 is similar to the process for an individual reactor 10. The process includes the steps of introducing liquid feed to a plurality of reactors 10, heating the liquid feed within each reactor 10, vaporizing the heated liquid feed within each reactor 10 to form a vapor and contacting, at predetermined reaction conditions, the vapor with catalyst 24 in each reactor 10 to form a product.

The liquid feed is introduced to each evaporation zone 18 in array 120 simultaneously through injectors 48 so that reactors 10 of array 120 are operating in parallel. The liquid feed in each reactor 10 is contacted with packing 76 and then heated within each reactor 10 until it is vaporized within evaporation zones 18. Evaporator heater 20 provides the heat for each reactor 10 in array 120 so that the liquid feed in each bed 78 reaches its bubble point very soon after it is injected into bed 78.

The vapor in each reactor 10 then passes into receptacle 22 of each reactor 10 through fluid permeable member 80. As with individual reactor 10, a gas feed may be introduced in some cases and contacted with catalyst 24 and vapor to react and form a product gas.

After passing through fluid permeable member 80 and into reaction zone 26 of each reactor 10, the vapor and the gas feed, if present, are heated to a predetermined temperature by reaction heater 108. A single reaction heater 108 may be used to provide the heat necessary to maintain a predetermined temperature within each of the reaction zones 26, or multiple reaction heaters 108 may be used to heat individual reaction zones 26, or blocks of reaction zones 26.

The temperature of catalyst 24 in each reaction zone 26 is constantly measured with a thermocouple 54. This temperature is then used to control the setting of reaction heater 108 of array 120, or of the individual corresponding heater for that particular reaction zone 26, or block of reaction zones 26 as described above.

After being heated to a predetermined temperature, the vapor, the gas feed and catalyst 24 are contacted in each reaction zone 26 of each reactor 10 in array 120 so that they react and form a product mixture of a product gas, byproducts and unreacted feeds. The product mixture then exits from each of the reactors 10 through a corresponding product conduit 40. As with a single reactor 10, each of the product mixtures may be diluted with a diluent gas that is mixed with the product mixtures in a corresponding mixing zone 110 after the product has been formed in each of the reaction zones 26.

It is preferred that the chemical composition of the liquid feed, the gas feed and the diluent gas be known and that the liquid feed, the gas feed and the diluent gas be introduced to each reactor 10 of array 120 in measured.

At least a portion of each of the product mixtures is sampled and analyzed by a corresponding analyzer 112 to determine its chemical composition so that the activity, feed conversion, major product and byproduct selectivities and yields for each catalyst 24 may be calculated.

Several advantages of the present invention are readily apparent. The evaporation zone is versatile because it allows liquid phase feeds to be fed as a gaseous fluid to a variety of different types of treatment zones. Feeds of different phases may be mixed and fed as a gaseous mixture to the treatment zone. For example, a liquid phase feed may be vaporized and combined with a gas phase feed to form a continuous supply of a gaseous mixture. With both the evaporation zone and the treatment zone being in the same process vessel any need to transport the gaseous feed through heat-traced conduits has been eliminated thereby minimizing the possibility of feed components condensing out of the gaseous mixture prior to encountering the treatment zone. In particular, the inventive evaporation zone can be located within a process vessel that can be easily and quickly assembled and disassembled using seals. The vaporization of the liquid feed is accomplished without compromising the seals that allow the process vessel to be easily assembled.

The present invention should not be limited to the above-described embodiments, but should be limited solely by the following claims.

What is claimed is:

1. A process vessel for evaporating a liquid feed and treating the resulting vapor comprising:
    an evaporation zone;
    a treatment zone;
    an insert containing at least one evaporation surface for evaporating feed and generating vapor, said insert positioned within the process vessel so that the evaporation surface is within the evaporation zone;
    an injector having an orifice, wherein said orifice is in the evaporation zone and the injector orifice and the evaporation surface are positioned relative to each other so as to prevent the formation of a drop at the orifice;
    a solids receptacle containing solid particles for treating the vapor, said solids receptacle positioned within the process vessel so that the solid particles are within the treatment zone;
    a housing having an inlet and an outlet and having the solids receptacle nested within the housing and the insert nested within the solids receptacle; and
    at least one heater associated with at least a portion of the process vessel.

2. A process vessel according to claim 1, wherein the evaporation surface is selected from the group consisting of a bed containing packing, a porous monolith, a plate, a cone, and combinations thereof.

3. A process vessel according to claim 1, wherein the insert is removable.

4. A process vessel according to claim 1, wherein the solids receptacle is removable.

5. A process vessel according to claim 1, further comprising a fluid permeable member attached to the receptacle to retain the solids but allow fluid to pass.

6. A process vessel according to claim 1, further comprising a fluid permeable member attached to the insert to retain the evaporation surface but allow fluid to pass.

7. A process vessel according to claim 1, further comprising an analyzer in fluid communication with the outlet of the housing.

8. A process vessel according to claim claim 1, wherein the heater is associated primarily with the evaporation zone and further comprising a second heater associated primarily with the treatment zone.

9. A process vessel according to claim 1, wherein said housing and said solids receptacle define a diluent inlet.

10. An array of process vessels for evaporating a liquid feed and treating the resulting vapor in combinatorial processes comprising a plurality of process vessels and a heater associated with a portion of the process vessels, each process vessel having:
    an evaporation zone;
    a treatment zone;
    an insert containing at least one evaporation surface, the insert being positioned within the process vessel so that the evaporation surface is within the evaporation zone;
    an injector having an orifice, wherein said orifice is in the evaporation zone and the injector orifice and the evaporation surface are positioned relative to each other so as to prevent the formation of a drop at the orifice;
    a solids receptacle containing solid particles for treating vapor, the solids receptacle being positioned within the process vessel so that the solid particles are within the treatment zone; and
    a housing having at least one inlet and at least one outlet and having the solids receptacle nested within the housing and the insert nested within the solids receptacle.

11. An array according to claim 10, wherein the inserts are removable.

12. An array according to claim 10, wherein the receptacles are removable.

13. An array according to claim 10, wherein the evaporation surfaces are selected from the group consisting of a bed containing packing, a porous monolith, a plate, a cone, and combinations thereof.

14. An array according to claim 10, wherein the housings and the solids receptacles define diluent inlets.

* * * * *